United States Patent
Li et al.

(10) Patent No.: US 11,447,570 B2
(45) Date of Patent: Sep. 20, 2022

(54) BINDING UNIT TARGETING FIBROBLAST ACTIVATION PROTEIN α AND APPLICATION THEREOF

(71) Applicant: CRAGE MEDICAL CO., LIMITED, Kowloon (CN)

(72) Inventors: Zonghai Li, Shanghai (CN); Peng Wang, Shanghai (CN)

(73) Assignee: CRAGE MEDICAL CO., LIMITED, Kowloon (CN)

( * ) Notice: Subject to any disclaimer, the term of this patent is extended or adjusted under 35 U.S.C. 154(b) by 0 days.

(21) Appl. No.: 16/765,100

(22) PCT Filed: Nov. 16, 2018

(86) PCT No.: PCT/CN2018/115945
§ 371 (c)(1),
(2) Date: May 18, 2020

(87) PCT Pub. No.: WO2019/096261
PCT Pub. Date: May 23, 2019

(65) Prior Publication Data
US 2020/0347151 A1    Nov. 5, 2020

(30) Foreign Application Priority Data
Nov. 17, 2017   (CN) .......................... 201711146783.4

(51) Int. Cl.
| | | |
|---|---|---|
| *A61K 39/395* | (2006.01) | |
| *A61K 39/00* | (2006.01) | |
| *C07K 16/40* | (2006.01) | |
| *C07K 19/00* | (2006.01) | |
| *C12N 15/62* | (2006.01) | |
| *C12N 15/86* | (2006.01) | |

(52) U.S. Cl.
CPC .............. *C07K 16/40* (2013.01); *C07K 19/00* (2013.01); *C12N 15/62* (2013.01); *C12N 15/86* (2013.01); *A61K 2039/505* (2013.01); *C07K 2317/565* (2013.01); *C07K 2317/622* (2013.01)

(58) Field of Classification Search
None
See application file for complete search history.

(56) References Cited

U.S. PATENT DOCUMENTS

2016/0326265 A1   11/2016 June et al.

FOREIGN PATENT DOCUMENTS

| CN | 103154038 A | 6/2013 |
|---|---|---|
| CN | 106349389 A | 1/2017 |
| CN | 107074975 A | 8/2017 |
| EP | 1806365 A1 | 7/2007 |
| WO | 9305804 A1 | 4/1993 |
| WO | 9413804 A1 | 6/1994 |
| WO | 02083171 A2 | 10/2002 |
| WO | 2016110598 A1 | 7/2016 |

OTHER PUBLICATIONS

Paul, Fundamental Immunology, 3rd Edition, 1993, pp. 292-295. (Year: 1993).*
Rudikoff et al Single amino acid substitution altering antigen-binding specificity. Proc Natl Acad Sci U S A. Mar. 1982;79(6):1979-83 (Year: 1982).*
Brown et al. Tolerance of single, but not multiple, amino acid replacements in antibody VH CDR2: a means of minimizing B cell wastage from somatic hypermutation? J. Immuno. May 1996, 3285-91. (Year: 1999).*
Vajdos et al. Comprehensive functional maps of the antigen-binding site of an anti-ErbB2 antibody obtained with shotgun scanning mutagenesis. J. Mol. Biol. 2002, Jul. 5, 320(2):415-28. (Year: 2002).*
Wang et al. Targeting Fibroblast Activation Protein in Tumor Stroma with Chimeric Antigen Receptor T Cells Can Inhibit Tumor Growth and Augment Host Immunity without Severe Toxicity. Cancer Immunol Res; 2(2); 154-66. (Year: 2013).*
International Search Report and Written Opinion issued in PCT/CN2018/115945, dated Feb. 19, 2019, with English translation, 18 pages provided.
International Preliminary Report on Patentability issued in PCT/CN2018/115945, dated May 19, 2020, With partial English translation, 4 pages provided.
Coloma et al., "Design and production of novel tetravalent bispecific antibodies", Nature Biotechnolgy, vol. 15, Feb. 1997, pp. 159-163, Cited in Specification.
Hofheinz et al., "Stromal Antigen Targeting by a Humanised Monoclonal Antibody: An Early Phase II Trial of Sibrotuzumab in Patients with Metastatic Colorectal Cancer", Onkologie, 2003; 26; pp. 44-48, Cited in Specification.
Holliger et al., "Diabodies": small bivalent and bispecific antibody fragments., Proc Natl Acad Sci U S A., Jul. 1993, vol. 90, pp. 6444-6448, Cited in Specification.
Cuesta et al., "Multivalent antibodies: when design surpasses evolution", Trends in Biotechnol, Jul. 2010; 28(7), pp. 355-362, Cited in Specification.
Cheng et al., "Tumors and Their Microenvironments: Tilling the Soil Commentary re: A. M. Scott et al., A Phase I Dose-Escalation Study of Sibrotuzumab in Patients with Advanced or Metastatic Fibroblast Activation Protein-positive Cancer. Clin. Cancer Res., 9: 1639-1647, 2003.", Jun. 2003, Clinical Cancer Research 9(5), pp. 1590-1595.

(Continued)

*Primary Examiner* — Maher M Haddad
(74) *Attorney, Agent, or Firm* — Hamre, Schumann, Mueller & Larson, P.C.

(57) ABSTRACT

A binding unit that specifically binds to fibroblast activation protein α (FAPα), a polynucleotide that encodes the binding unit, a vector that comprises the polynucleotide and a host cell, a method for use in producing the antigen-binding unit and a method for treating a disease by using the FAPα-specific binding unit; the binding unit that specifically binds to FAPα may efficiently bind to tumor cells that express FAPα, and immune effector cells comprising the binding unit exhibit significant killing capabilities against tumor cells that express FAP.

12 Claims, 8 Drawing Sheets

Specification includes a Sequence Listing.

(56) References Cited

OTHER PUBLICATIONS

Tomlinson et al., "Methods for generating multivalent and bispecific antibody fragments", Methods in Enzymology, vol. 326, 2000, pp. 461-479, Cited in Specification.

Extended European Search Report; European Patent Application No. 18878002.7, dated Sep. 24, 2021 (10 pages).

Scarfo et al., "Current approaches to increase CAR T cell potency in solid tumors: targeting the tumor microenvironment", Journal for Immunotherapy of Cancer, vol. 5, No. 1, pp. 1-8, Mar. 21, 2017.

Yong et al., "CAR T-cell therapy of solid tumors", Immunology and Cell Biology, vol. 95, No. 4, pp. 356-353, Dec. 22, 2016.

Kumar et al., "Cancer-Associated Fibroblasts Neutralize the Antitumor Effect of CSF1 Receptor Blockade by Inducing PMN-MDSC Infiltration of Tumors", Cancer Cell, vol. 32, No. 5, p. 654, Nov. 13, 2017.

\* cited by examiner

Fig.5

1. 3T3-mFAP mixed clone
2. 3T3 cells
3. HT1080-huFAP mixed clone
4. HT1080 cells

SEQUENCE LISTING

```
<160> NUMBER OF SEQ ID NOS: 48

<210> SEQ ID NO 1
<211> LENGTH: 5
<212> TYPE: PRT
<213> ORGANISM: Artificial sequence
<220> FEATURE:
<223> OTHER INFORMATION: 10A4 HCDR1

<400> SEQUENCE: 1

Ser Tyr Ala Ile Ser
1               5

<210> SEQ ID NO 2
<211> LENGTH: 17
<212> TYPE: PRT
<213> ORGANISM: Artificial sequence
<220> FEATURE:
<223> OTHER INFORMATION: 10A4 HCDR2

<400> SEQUENCE: 2

Gly Ile Ile Pro Ile Phe Gly Thr Ala Asn Tyr Ala Gln Lys Phe Gln
1               5                   10                  15

Gly

<210> SEQ ID NO 3
<211> LENGTH: 7
<212> TYPE: PRT
<213> ORGANISM: Artificial sequence
<220> FEATURE:
<223> OTHER INFORMATION: 10A4 HCDR3

<400> SEQUENCE: 3

Asp Ala Ala Asp Arg Asp Tyr
1               5

<210> SEQ ID NO 4
<211> LENGTH: 16
<212> TYPE: PRT
<213> ORGANISM: Artificial sequence
```

```
<220> FEATURE:
<223> OTHER INFORMATION: 10A4 LCDR1

<400> SEQUENCE: 4

Arg Ser Ser Gln Ser Leu Leu His Ser Asn Gly Tyr Asn Tyr Leu Asp
1               5                   10                  15

<210> SEQ ID NO 5
<211> LENGTH: 7
<212> TYPE: PRT
<213> ORGANISM: Artificial sequence
<220> FEATURE:
<223> OTHER INFORMATION: 10A4 LCDR2

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Artificial sequence
<220> FEATURE:
<223> OTHER INFORMATION: 10A4 LCDR3

<400> SEQUENCE: 6

Gln Gln Arg Asn Asn Lys Asn Arg Thr
1               5

<210> SEQ ID NO 7
<211> LENGTH: 5
<212> TYPE: PRT
<213> ORGANISM: Artificial sequence
<220> FEATURE:
<223> OTHER INFORMATION: 1A7 HCDR1

<400> SEQUENCE: 7

Pro Tyr Thr Ile Ser
1               5

<210> SEQ ID NO 8
<211> LENGTH: 17
<212> TYPE: PRT
<213> ORGANISM: Artificial sequence
<220> FEATURE:
<223> OTHER INFORMATION: 1A7 HCDR2

<400> SEQUENCE: 8

Gly Ile Val Pro Asn Val Gly Val Ala Thr Tyr Ala Gln Lys Phe Gln
1               5                   10                  15

Gly

<210> SEQ ID NO 9
<211> LENGTH: 16
<212> TYPE: PRT
<213> ORGANISM: Artificial sequence
<220> FEATURE:
<223> OTHER INFORMATION: 8E3 LCDR1

<400> SEQUENCE: 9

Arg Ser Ser Gln Ser Leu Leu His Pro Asn Gly Phe Asn His Leu Tyr
1               5                   10                  15

<210> SEQ ID NO 10
<211> LENGTH: 7
<212> TYPE: PRT
```

```
<213> ORGANISM: Artificial sequence
<220> FEATURE:
<223> OTHER INFORMATION: 8E3 LCDR2

<400> SEQUENCE: 10

Val Gly Gly Asn Arg Ala Ser
1               5

<210> SEQ ID NO 11
<211> LENGTH: 116
<212> TYPE: PRT
<213> ORGANISM: Artificial sequence
<220> FEATURE:
<223> OTHER INFORMATION: 10A4 VH

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Asp Arg Asp Tyr Trp Gly Gln Gly Thr Thr Val
            100                 105                 110

Thr Val Ser Ser
        115

<210> SEQ ID NO 12
<211> LENGTH: 348
<212> TYPE: DNA
<213> ORGANISM: Artificial sequence
<220> FEATURE:
<223> OTHER INFORMATION: 10A4 VH

<400> SEQUENCE: 12
caggtgcaat tggtgcagtc tggggctgag gtgaagaagc ctgggtcctc ggtgaaggtc     60
tcctgcaagg cctccggagg cacattcagc agctacgcta taagctgggt gcgacaggcc    120
cctggacaag gctcgagtg gatgggaggg atcatcccta tctttggtac agcaaactac    180
gcacagaagt tccagggcag ggtcaccatt actgcagaca atccacgag cacagcctac    240 atggagctga gcagcctgag atctgaggac accgccgtgt attactgtgc gagagatgct    300
gctgataggg actactgggg ccaagggacc accgtgaccg tctcctca              348

<210> SEQ ID NO 13
<211> LENGTH: 113
<212> TYPE: PRT
<213> ORGANISM: Artificial sequence
<220> FEATURE:
<223> OTHER INFORMATION: 10A4 VL

<400> SEQUENCE: 13

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

```
                    20                  25                  30
Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Arg
                85                  90                  95

Asn Asn Lys Asn Arg Thr Phe Gly Gln Gly Thr Lys Val Glu Ile Lys
                100                 105                 110

Arg

<210> SEQ ID NO 14
<211> LENGTH: 339
<212> TYPE: DNA
<213> ORGANISM: Artificial sequence
<220> FEATURE:
<223> OTHER INFORMATION: 10A4 VL

<400> SEQUENCE: 14
gatattgtta tgactcaatc tccactgtct ctgccggtga ctccaggcga accggcgagc    60
atttcttgcc gttccagcca gtctctgctg cactccaacg ctacaacta tctcgattgg   120 tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgtc agcagcgtaa taataagaat   300
cgtacttttg gtcaaggcac caaggtcgaa attaaacgt                          339

<210> SEQ ID NO 15
<211> LENGTH: 116
<212> TYPE: PRT
<213> ORGANISM: Artificial sequence
<220> FEATURE:
<223> OTHER INFORMATION: 1A7 VH

<400> SEQUENCE: 15

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Pro Tyr
                20                  25                  30

Thr Ile Ser Trp Val Arg Gln Ala Pro Gly Gln Gly Leu Glu Trp Met
            35                  40                  45

Gly Gly Ile Val Pro Asn Val Gly Val Ala Thr Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ala Ala Asp Arg Asp Tyr Trp Gly Gln Gly Thr Thr Val
                100                 105                 110

Thr Val Ser Ser
           115

<210> SEQ ID NO 16
<211> LENGTH: 348
<212> TYPE: DNA
```

```
<213> ORGANISM: Artificial sequence
<220> FEATURE:
<223> OTHER INFORMATION: 1A7 VH

<400> SEQUENCE: 16
caggtgcaat tggtgcagtc tggggctgag gtgaagaagc ctgggtcctc ggtgaaggtc      60
tcctgcaagg cctccggagg cacattcagc ccctacacta taagctgggt gcgacaggcc     120
cctggacaag gctcgagtg gatgggaggg atcgtcccta tgttggtgt agcaacctac       180 gcacagaagt tccagggcag ggtcaccatt actgcagaca atccacgag cacagcctac      240 atggagctga gcagcctgag atctgaggac accgccgtgt attactgtgc gagagatgct    300
gctgataggg actactgggg ccaagggacc accgtgaccg tctcctca                 348

<210> SEQ ID NO 17
<211> LENGTH: 113
<212> TYPE: PRT
<213> ORGANISM: Artificial sequence
<220> FEATURE:
<223> OTHER INFORMATION: 8E3 VL

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Pro
            20                  25                  30

Asn Gly Phe Asn His Leu Tyr Trp Tyr Leu Gln Lys Pro Gly Gln Ser
        35                  40                  45

Pro Gln Leu Leu Ile Tyr Val Gly Gly Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Arg
                85                  90                  95

Asn Asn Lys Asn Arg Thr Phe Gly Gln Gly Thr Lys Val Glu Ile Lys
            100                 105                 110

Arg

<210> SEQ ID NO 18
<211> LENGTH: 339
<212> TYPE: DNA
<213> ORGANISM: Artificial sequence
<220> FEATURE:
<223> OTHER INFORMATION: 8E3 VL

<400> SEQUENCE: 18
gatattgtta tgactcaatc tccactgtct ctgccggtga ctccaggcga accggcgagc      60
atttcttgcc gttccagcca gtctctgctt caccccaacg gcttcaacca tctctattgg     120
tacctgcaaa aaccgggtca gagccctcag ctgctgatct acgtgggggg taaccgcgct     180
tccggtgtac cggaccgttt cagcggctct ggatccggca ccgatttcac gttgaaaatc     240
agccgtgttg aagcagaaga cgtgggcgtt tattactgtc agcagcgtaa taataagaat    300
cgtacttttg gtcaaggcac caaggtcgaa attaaacgt                            339

<210> SEQ ID NO 19
<211> LENGTH: 743
<212> TYPE: PRT
<213> ORGANISM: Artificial sequence
<220> FEATURE:
```

<223> OTHER INFORMATION: human FAP alpha_His

<400> SEQUENCE: 19

```
Leu Arg Pro Ser Arg Val His Asn Ser Glu Glu Asn Thr Met Arg Ala
1               5                   10                  15

Leu Thr Leu Lys Asp Ile Leu Asn Gly Thr Phe Ser Tyr Lys Thr Phe
            20                  25                  30

Phe Pro Asn Trp Ile Ser Gly Gln Glu Tyr Leu His Gln Ser Ala Asp
        35                  40                  45

Asn Asn Ile Val Leu Tyr Asn Ile Glu Thr Gly Gln Ser Tyr Thr Ile
    50                  55                  60

Leu Ser Asn Arg Thr Met Lys Ser Val Asn Ala Ser Asn Tyr Gly Leu
65                  70                  75                  80

Ser Pro Asp Arg Gln Phe Val Tyr Leu Glu Ser Asp Tyr Ser Lys Leu
                85                  90                  95

Trp Arg Tyr Ser Tyr Thr Ala Thr Tyr Tyr Ile Tyr Asp Leu Ser Asn
            100                 105                 110

Gly Glu Phe Val Arg Gly Asn Glu Leu Pro Arg Pro Ile Gln Tyr Leu
        115                 120                 125

Cys Trp Ser Pro Val Gly Ser Lys Leu Ala Tyr Val Tyr Gln Asn Asn
    130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
        195                 200                 205

Ile Ala Tyr Ser Tyr Tyr Gly Asp Glu Gln Tyr Pro Arg Thr Ile Asn
    210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
        275                 280                 285

Asn Val Ser Val Leu Ser Ile Cys Asp Phe Arg Glu Asp Trp Gln Thr
    290                 295                 300

Trp Asp Cys Pro Lys Thr Gln Glu His Ile Glu Glu Ser Arg Thr Gly
305                 310                 315                 320

Trp Ala Gly Gly Phe Phe Val Ser Thr Pro Val Phe Ser Tyr Asp Ala
                325                 330                 335

Ile Ser Tyr Tyr Lys Ile Phe Ser Asp Lys Asp Gly Tyr Lys His Ile
            340                 345                 350

His Tyr Ile Lys Asp Thr Val Glu Asn Ala Ile Gln Ile Thr Ser Gly
        355                 360                 365

Lys Trp Glu Ala Ile Asn Ile Phe Arg Val Thr Gln Asp Ser Leu Phe
    370                 375                 380

Tyr Ser Ser Asn Glu Phe Glu Tyr Pro Gly Arg Arg Asn Ile Tyr
385                 390                 395                 400
```

```
Arg Ile Ser Ile Gly Ser Tyr Pro Pro Ser Lys Lys Cys Val Thr Cys
                405                 410                 415
His Leu Arg Lys Glu Arg Cys Gln Tyr Tyr Thr Ala Ser Phe Ser Asp
        420                 425                 430
Tyr Ala Lys Tyr Tyr Ala Leu Val Cys Tyr Gly Pro Gly Ile Pro Ile
            435                 440                 445
Ser Thr Leu His Asp Gly Arg Thr Asp Gln Glu Ile Lys Ile Leu Glu
        450                 455                 460
Glu Asn Lys Glu Leu Glu Asn Ala Leu Lys Asn Ile Gln Leu Pro Lys
465                 470                 475                 480
Glu Glu Ile Lys Lys Leu Glu Val Asp Glu Ile Thr Leu Trp Tyr Lys
                485                 490                 495
Met Ile Leu Pro Pro Gln Phe Asp Arg Ser Lys Lys Tyr Pro Leu Leu
            500                 505                 510
Ile Gln Val Tyr Gly Gly Pro Cys Ser Gln Ser Val Arg Ser Val Phe
        515                 520                 525
Ala Val Asn Trp Ile Ser Tyr Leu Ala Ser Lys Glu Gly Met Val Ile
    530                 535                 540
Ala Leu Val Asp Gly Arg Gly Thr Ala Phe Gln Gly Asp Lys Leu Leu
545                 550                 555                 560
Tyr Ala Val Tyr Arg Lys Leu Gly Val Tyr Glu Val Glu Asp Gln Ile
                565                 570                 575
Thr Ala Val Arg Lys Phe Ile Glu Met Gly Phe Ile Asp Glu Lys Arg
            580                 585                 590
Ile Ala Ile Trp Gly Trp Ser Tyr Gly Gly Tyr Val Ser Ser Leu Ala
        595                 600                 605
Leu Ala Ser Gly Thr Gly Leu Phe Lys Cys Gly Ile Ala Val Ala Pro
    610                 615                 620
Val Ser Ser Trp Glu Tyr Tyr Ala Ser Val Tyr Thr Glu Arg Phe Met
625                 630                 635                 640
Gly Leu Pro Thr Lys Asp Asp Asn Leu Glu His Tyr Lys Asn Ser Thr
                645                 650                 655
Val Met Ala Arg Ala Glu Tyr Phe Arg Asn Val Asp Tyr Leu Leu Ile
            660                 665                 670
His Gly Thr Ala Asp Asp Asn Val His Phe Gln Asn Ser Ala Gln Ile
        675                 680                 685
Ala Lys Ala Leu Val Asn Ala Gln Val Asp Phe Gln Ala Met Trp Tyr
    690                 695                 700
Ser Asp Gln Asn His Gly Leu Ser Gly Leu Ser Thr Asn His Leu Tyr
705                 710                 715                 720
Thr His Met Thr His Phe Leu Lys Gln Cys Phe Ser Leu Ser Asp Gly
                725                 730                 735
Ser His His His His His His
            740

<210> SEQ ID NO 20
<211> LENGTH: 2229
<212> TYPE: DNA
<213> ORGANISM: Artificial sequence
<220> FEATURE:
<223> OTHER INFORMATION: human FAP alpha_His

<400> SEQUENCE: 20
ctgcggccca gccgggtgca caacagcgag gagaacacca tgcgggccct gaccctgaag      60
gacatcctga acggcacctt cagctacaag accttcttcc ccaactggat cagcggccag     120
```

```
gagtacctgc accagagcgc cgacaacaac atcgtgctgt acaacatcga gaccggccag      180
agctacacca tcctgagcaa ccggaccatg aagagcgtga acgccagcaa ctacggcctg      240
agccccgacc ggcagttcgt gtacctggag agcgactaca gcaagctgtg gcggtacagc      300
tacaccgcca cctactacat ctacgacctg agcaacggcg agttcgtgcg gggcaacgag      360
ctgccccggc ccatccagta cctgtgctgg agcccgtggg gcagcaagct ggcctacgtg      420
taccagaaca acatctacct gaagcagcgg cccggcgacc cccccttcca gatcaccttc      480
aacggccggg agaacaagat cttcaacggc atccccgact gggtgtacga ggaggagatg      540
ctggccacca agtacgccct ggtggagc    ccaacggca agttcctggc ctacgccgag      600
ttcaacgaca ccgacatccc cgtgatcgcc tacagctact acggcgacga gcagtacccc      660
cggaccatca acatccccta ccccaaggcc ggcgccaaga accccgtggt gcggatcttc      720
atcatcgaca ccacctaccc cgcctacgtg gcccccagg aggtgcccgt gcccgccatg      780
atcgccagca gcgactacta cttcagctgg ctgacctggg tgaccgacga gcgggtgtgc      840
ctgcagtggc tgaagcgggt gcagaacgtg agcgtgctga gcatctgcga cttccgggag      900
gactggcaga cctgggactg ccccaagacc caggagcaca tcgaggagag ccggaccggc      960
tgggccggcg gcttcttcgt gagcaccccc gtgttcagct acgacgccat cagctactac     1020
aagatcttca gcgacaagga cggctacaag cacatccact acatcaagga caccgtggag     1080
aacgccatcc agatcaccag cggcaagtgg gaggccatca acatcttccg ggtgacccag     1140
gacagcctgt tctacagcag caacgagttc gaggagtacc ccggccggcg gaacatctac     1200
cggatcagca tcggcagcta cccccccagc aagaagtgcg tgacctgcca cctgcggaag     1260
gagcggtgcc agtactacac cgccagcttc agcgactacg ccaagtacta cgccctggtg     1320
tgctacggcc ccggcatccc catcagcacc ctgcacgacg ccggaccga ccaggagatc     1380 aagatcctgg aggagaacaa ggagctggag aacgccctga gaacatcca gctgcccaag     1440 gaggagatca agaagctgga ggtggacgag atcaccctgt ggtacaagat gatcctgccc     1500
ccccagttcg accggagcaa gaagtacccc ctgctgatcc aggtgtacgg cggcccctgc     1560
agccagagcg tgcggagcgt gttcgccgtg aactggatca gctacctggc cagcaaggag     1620
ggcatggtga tcgccctggt ggacggccgg ggcaccgcct tccagggcga caagctgctg     1680
tacgccgtgt accggaagct gggcgtgtac gaggtggagg accagatcac cgccgtgcgg     1740
aagttcatcg agatgggctt catcgacgag aagcggatcg ccatctgggg ctggagctac     1800
ggcggctacg tgagcagcct ggccctggcc agcggcaccg gctgttcaa gtgcggcatc     1860 gccgtggccc ccgtgagcag ctgggagtac tacgccagcg tgtacaccga gcggttcatg     1920
ggcctgccca ccaaggacga caacctggag cactacaaga acagcaccgt gatggcccgg     1980
gccgagtact ccggaacgt ggactacctg ctgatccacg gcaccgccga cgacaacgtg     2040
cacttccaga cagcgccca gatcgccaag gccctggtga acgcccaggt ggacttccag     2100
gccatgtggt acagcgacca gaaccacggc ctgagcggcc tgagcaccaa ccacctgtac     2160
acccacatga cccacttcct gaagcagtgc ttcagcctga gcgacggatc ccatcatcac     2220
catcatcat                                                                2229
```

<210> SEQ ID NO 21
<211> LENGTH: 744
<212> TYPE: PRT
<213> ORGANISM: Artificial sequence
<220> FEATURE:

<223> OTHER INFORMATION: mouse FAP alpha_His

<400> SEQUENCE: 21

```
Leu Arg Pro Ser Arg Val Tyr Lys Pro Glu Gly Asn Thr Lys Arg Ala
1               5                   10                  15

Leu Thr Leu Lys Asp Ile Leu Asn Gly Thr Phe Ser Tyr Lys Thr Tyr
            20                  25                  30

Phe Pro Asn Trp Ile Ser Glu Gln Glu Tyr Leu His Gln Ser Glu Asp
        35                  40                  45

Asp Asn Ile Val Phe Tyr Asn Ile Glu Thr Arg Glu Ser Tyr Ile Ile
    50                  55                  60

Leu Ser Asn Ser Thr Met Lys Ser Val Asn Ala Thr Ser Tyr Gly Leu
65                  70                  75                  80

Ser Pro Asp Arg Gln Phe Val Tyr Leu Glu Ser Asp Tyr Ser Lys Leu
                85                  90                  95

Trp Arg Tyr Ser Tyr Thr Ala Thr Tyr Tyr Ile Tyr Asp Leu Gln Asn
            100                 105                 110

Gly Glu Phe Val Arg Gly Tyr Glu Leu Pro Arg Pro Ile Gln Tyr Leu
        115                 120                 125

Cys Trp Ser Pro Val Gly Ser Lys Leu Ala Tyr Val Tyr Gln Asn Asn
130                 135                 140

Ile Tyr Leu Lys Gln Arg Pro Gly Asp Pro Pro Phe Gln Ile Thr Tyr
145                 150                 155                 160

Thr Gly Arg Glu Asn Arg Ile Phe Asn Gly Ile Pro Asp Trp Val Tyr
                165                 170                 175

Glu Glu Glu Met Leu Ala Thr Lys Tyr Ala Leu Trp Trp Ser Pro Asp
            180                 185                 190

Gly Lys Phe Leu Ala Tyr Val Glu Phe Asn Asp Ser Asp Ile Pro Ile
        195                 200                 205

Ile Ala Tyr Ser Tyr Tyr Gly Asp Gly Gln Tyr Pro Arg Thr Ile Asn
210                 215                 220

Ile Pro Tyr Pro Lys Ala Gly Ala Lys Asn Pro Val Val Arg Val Phe
225                 230                 235                 240

Ile Val Asp Thr Thr Tyr Pro His His Val Gly Pro Met Glu Val Pro
                245                 250                 255

Val Pro Glu Met Ile Ala Ser Ser Asp Tyr Tyr Phe Ser Trp Leu Thr
            260                 265                 270

Trp Val Ser Ser Glu Arg Val Cys Leu Gln Trp Leu Lys Arg Val Gln
        275                 280                 285

Asn Val Ser Val Leu Ser Ile Cys Asp Phe Arg Glu Asp Trp His Ala
290                 295                 300

Trp Glu Cys Pro Lys Asn Gln Glu His Val Glu Glu Ser Arg Thr Gly
305                 310                 315                 320

Trp Ala Gly Gly Phe Phe Val Ser Thr Pro Ala Phe Ser Gln Asp Ala
                325                 330                 335

Thr Ser Tyr Tyr Lys Ile Phe Ser Lys Asp Gly Tyr Lys His Ile
            340                 345                 350

His Tyr Ile Lys Asp Thr Val Glu Asn Ala Ile Gln Ile Thr Ser Gly
        355                 360                 365

Lys Trp Glu Ala Ile Tyr Ile Phe Arg Val Thr Gln Asp Ser Leu Phe
        370                 375                 380

Tyr Ser Ser Asn Glu Phe Glu Gly Tyr Pro Gly Arg Arg Asn Ile Tyr
385                 390                 395                 400
```

-continued

```
Arg Ile Ser Ile Gly Asn Ser Pro Pro Ser Lys Lys Cys Val Thr Cys
                405                 410                 415

His Leu Arg Lys Glu Arg Cys Gln Tyr Tyr Thr Ala Ser Phe Ser Tyr
        420                 425                 430

Lys Ala Lys Tyr Tyr Ala Leu Val Cys Tyr Gly Pro Gly Leu Pro Ile
        435                 440                 445

Ser Thr Leu His Asp Gly Arg Thr Asp Gln Glu Ile Gln Val Leu Glu
    450                 455                 460

Glu Asn Lys Glu Leu Glu Asn Ser Leu Arg Asn Ile Gln Leu Pro Lys
465                 470                 475                 480

Val Glu Ile Lys Lys Leu Lys Asp Gly Gly Leu Thr Phe Trp Tyr Lys
                485                 490                 495

Met Ile Leu Pro Pro Gln Phe Asp Arg Ser Lys Lys Tyr Pro Leu Leu
            500                 505                 510

Ile Gln Val Tyr Gly Gly Pro Cys Ser Gln Ser Val Lys Ser Val Phe
        515                 520                 525

Ala Val Asn Trp Ile Thr Tyr Leu Ala Ser Lys Glu Gly Ile Val Ile
    530                 535                 540

Ala Leu Val Asp Gly Arg Gly Thr Ala Phe Gln Gly Asp Lys Phe Leu
545                 550                 555                 560

His Ala Val Tyr Arg Lys Leu Gly Val Tyr Glu Val Glu Asp Gln Leu
                565                 570                 575

Thr Ala Val Arg Lys Phe Ile Glu Met Gly Phe Ile Asp Glu Glu Arg
            580                 585                 590

Ile Ala Ile Trp Gly Trp Ser Tyr Gly Gly Tyr Val Ser Ser Leu Ala
        595                 600                 605

Leu Ala Ser Gly Thr Gly Leu Phe Lys Cys Gly Ile Ala Val Ala Pro
    610                 615                 620

Val Ser Ser Trp Glu Tyr Tyr Ala Ser Ile Tyr Ser Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
            660                 665                 670

His Gly Thr Ala Asp Asp Asn Val His Phe Gln Asn Ser Ala Gln Ile
        675                 680                 685

Ala Lys Ala Leu Val Asn Ala Gln Val Asp Phe Gln Ala Met Trp Tyr
    690                 695                 700

Ser Asp Gln Asn His Gly Ile Ser Ser Gly Arg Ser Gln Asn His Leu
705                 710                 715                 720

Tyr Thr His Met Thr His Phe Leu Lys Gln Cys Phe Ser Leu Ser Asp
                725                 730                 735

Gly Ser His His His His His His
            740
```

<210> SEQ ID NO 22
<211> LENGTH: 2232
<212> TYPE: DNA
<213> ORGANISM: Artificial sequence
<220> FEATURE:
<223> OTHER INFORMATION: mouse FAP alpha_His

<400> SEQUENCE: 22

```
ctgcggccca gccgggtgta caagcccgag ggcaacacca agcgggccct gaccctgaag    60
gacatcctga acggcacctt cagctacaag acctacttcc ccaactggat cagcgagcag   120
```

```
gagtacctgc accagagcga ggacgacaac atcgtgttct acaacatcga gacccgggag      180
agctacatca tcctgagcaa cagcaccatg aagagcgtga acgccaccga ctacggcctg      240
agccccgacc ggcagttcgt gtacctggag agcgactaca gcaagctgtg gcggtacagc      300
tacaccgcca cctactacat ctacgacctg cagaacggcg agttcgtgcg gggctacgag      360
ctgccccggc ccatccagta cctgtgctgg agcccgtgg gcagcaagct ggcctacgtg       420
taccagaaca acatctacct gaagcagcgg cccggcgacc cccccttcca gatcacctac      480
accggccggg agaaccggat cttcaacggc atccccgact gggtgtacga ggaggagatg      540
ctggccacca agtacgccct gtggtggagc cccgacggca gttcctggc ctacgtggag       600 ttcaacgaca gcgacatccc catcatcgcc tacagctact acggcgacgg ccagtacccc      660
cggaccatca acatcccta ccccaaggcc ggcgccaaga accccgtggt gcgggtgttc       720
atcgtggaca ccacctaccc ccaccacgtg ggccccatgg aggtgcccgt gcccgagatg      780
atcgccagca gcgactacta cttcagctgg ctgacctggg tgagcagcga gcgggtgtgc      840
ctgcagtggc tgaagcgggt gcagaacgtg agcgtgctga gcatctgcga cttccgggag      900
gactggcacg cctgggagtg ccccaagaac caggagcacg tggaggagag ccggaccggc      960
tgggccggcg gcttcttcgt gagcaccccc gccttcagcc aggacgccac cagctactac     1020
aagatcttca gcgacaagga cggctacaag cacatccact acatcaagga caccgtggag     1080
aacgccatcc agatcaccag cggcaagtgg gaggccatct acatcttccg ggtgacccag     1140
gacagcctgt tctacagcag caacgagttc gagggctacc ccggccgcgc gaacatctac     1200
cggatcagca tcggcaacag cccccccagc aagaagtgcg tgacctgcca cctgcggaag     1260
gagcggtgcc agtactacac cgccagcttc agctacaagg ccaagtacta cgccctggtg     1320
tgctacggcc ccggcctgcc catcagcacc ctgcacgacg ccggaccga ccaggagatc      1380 caggtgctgg aggagaacaa ggagctggag aacagcctgc ggaacatcca gctgcccaag     1440
gtggagatca agaagctgaa ggacggcggc ctgaccttct ggtacaagat gatcctgccc     1500 cccccagttcg accggagcaa gaagtacccc ctgctgatcc aggtgtacgg cggcccctgc    1560
agccagagcg tgaagagcgt gttcgccgtg aactggatca cctacctggc cagcaaggag     1620
ggcatcgtga tcgccctggt ggacggccgg ggcaccgcct tccagggcga caagttcctg     1680
cacgccgtgt accggaagct gggcgtgtac gaggtggagg accagctgac cgccgtgcgg     1740
aagttcatcg agatgggctt catcgacgag gagcggatcg ccatctgggg ctggagctac     1800
ggcggctacg tgagcagcct ggccctggcc agcggcaccg cctgttcaa gtgcggcatc      1860 gccgtggccc ccgtgagcag ctgggagtac tacgccagca tctacagcga gcggttcatg     1920
ggcctgccca ccaaggacga caacctggag cactacaaga acagcaccgt gatggcccgg     1980
gccgagtact tccggaacgt ggactacctg ctgatccacg gcaccgccga cgacaacgtg     2040
cacttccaga cagcgccca gatcgccaag gccctggtga cgcccaggt ggacttccag       2100 gccatgtggt acagcgacca gaaccacggc atcagcagcg gccggagcca gaaccacctg     2160
tacacccaca tgacccactt cctgaagcag tgcttcagcc tgagcgacgg atcccatcat     2220
caccatcatc at                                                        2232
```

<210> SEQ ID NO 23
<211> LENGTH: 244
<212> TYPE: PRT
<213> ORGANISM: Artificial sequence
<220> FEATURE:

<223> OTHER INFORMATION: 10A4 scFv

<400> SEQUENCE: 23

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Gly | Thr | Phe | Ser | Ser | Tyr |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | | 35 | | | | | 40 | | | | | 45 | | |
| Gly | Gly | Ile | Ile | Pro | Ile | Phe | Gly | Thr | Ala | Asn | Tyr | Ala | Gln | Lys | Phe |
| | 50 | | | | | 55 | | | | | 60 | | | | |
| Gln | Gly | Arg | Val | Thr | Ile | Thr | Ala | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Asp | Ala | Ala | Asp | Arg | Asp | Tyr | Trp | Gly | Gln | Gly | Thr | Thr | Val |
| | | | 100 | | | | | 105 | | | | | 110 | | |
| Thr | Val | Ser | Ser | Gly | Gly | Gly | Gly | Ser | Gly | Gly | Gly | Gly | Ser | Gly | Gly |
| | | | 115 | | | | | 120 | | | | | 125 | | |
| Gly | Gly | Ser | Asp | Ile | Val | Met | Thr | Gln | Ser | Pro | Leu | Ser | Leu | Pro | Val |
| | 130 | | | | | 135 | | | | | 140 | | | | |
| Thr | Pro | Gly | Glu | Pro | Ala | Ser | Ile | Ser | Cys | Arg | Ser | Ser | Gln | Ser | Leu |
| 145 | | | | | 150 | | | | | 155 | | | | | 160 |
| Leu | His | Ser | Asn | Gly | Tyr | Asn | Tyr | Leu | Asp | Trp | Tyr | Leu | Gln | Lys | Pro |
| | | | | 165 | | | | | 170 | | | | | 175 | |
| Gly | Gln | Ser | Pro | Gln | Leu | Leu | Ile | Tyr | Leu | Gly | Ser | Asn | Arg | Ala | Ser |
| | | | 180 | | | | | 185 | | | | | 190 | | |
| Gly | Val | Pro | Asp | Arg | Phe | Ser | Gly | Ser | Gly | Ser | Gly | Thr | Asp | Phe | Thr |
| | | | 195 | | | | | 200 | | | | | 205 | | |
| Leu | Lys | Ile | Ser | Arg | Val | Glu | Ala | Glu | Asp | Val | Gly | Val | Tyr | Tyr | Cys |
| | 210 | | | | | 215 | | | | | 220 | | | | |
| Gln | Gln | Arg | Asn | Asn | Lys | Asn | Arg | Thr | Phe | Gly | Gln | Gly | Thr | Lys | Val |
| 225 | | | | | 230 | | | | | 235 | | | | | 240 |
| Glu | Ile | Lys | Arg | | | | | | | | | | | | |

<210> SEQ ID NO 24
<211> LENGTH: 732
<212> TYPE: DNA
<213> ORGANISM: Artificial sequence
<220> FEATURE:
<223> OTHER INFORMATION: 10A4 scFv

<400> SEQUENCE: 24

| | | | | | |
|---|---|---|---|---|---|
| caggtgcaat | tggtgcagtc | tggggctgag | gtgaagaagc | ctgggtcctc | ggtgaaggtc | 60 |
| tcctgcaagg | cctccggagg | cacattcagc | agctacgcta | taagctgggt | gcgacaggcc | 120 |
| cctggacaag | ggctcgagtg | gatgggaggg | atcatcccta | tctttggtac | agcaaactac | 180 |
| gcacagaagt | tccagggcag | ggtcaccatt | actgcagaca | aatccacgag | cacagcctac | 240 |
| atggagctga | gcagcctgag | atctgaggac | accgccgtgt | attactgtgc | gagagatgct | 300 |
| gctgataggg | actactgggg | ccaagggacc | accgtgaccg | tctcctcagg | tggaggcggt | 360 |
| tcaggcggag | gtggttctgg | cggtggcgga | tcggatattg | ttatgactca | atctccactg | 420 |
| tctctgccgg | tgactccagg | cgaaccggcg | agcatttctt | gccgttccag | ccagtctctg | 480 |
| ctgcactcca | acggctacaa | ctatctcgat | tggtacctgc | aaaaaccggg | tcagagccct | 540 |

```
cagctgctga tctacctggg ctctaaccgc gcttccggtg taccggaccg tttcagcggc    600
tctggatccg gcaccgattt cacgttgaaa tcagccgtg ttgaagcaga agacgtgggc    660
gtttattact gtcagcagcg taataataag aatcgtactt ttggtcaagg caccaaggtc    720
gaaattaaac gt                                                       732
```

\<210\> SEQ ID NO 25
\<211\> LENGTH: 244
\<212\> TYPE: PRT
\<213\> ORGANISM: Artificial sequence
\<220\> FEATURE:
\<223\> OTHER INFORMATION: 1A7 scFv

\<400\> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Pro Tyr
            20                  25                  30

Thr Ile Ser Trp Val Arg Gln Ala Pro Gly Gln Gly Leu Glu Trp Met
        35                  40                  45

Gly Gly Ile Val Pro Asn Val Gly Val Ala Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Asp Arg Asp Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Pro Leu Ser Leu Pro Val
    130                 135                 140

Thr Pro Gly Glu Pro Ala Ser Ile Ser Cys Arg Ser Gln Ser Leu
145                 150                 155                 160

Leu His Ser Asn Gly Tyr Asn Tyr Leu Asp Trp Tyr Leu Gln Lys Pro
                165                 170                 175

Gly Gln Ser Pro Gln Leu Leu Ile Tyr Leu Gly Ser Asn Arg Ala Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Val Tyr Tyr Cys
    210                 215                 220

Gln Gln Arg Asn Asn Lys Asn Arg Thr Phe Gly Gln Gly Thr Lys Val
225                 230                 235                 240

Glu Ile Lys Arg
```

\<210\> SEQ ID NO 26
\<211\> LENGTH: 732
\<212\> TYPE: DNA
\<213\> ORGANISM: Artificial sequence
\<220\> FEATURE:
\<223\> OTHER INFORMATION: 1A7 scFv

\<400\> SEQUENCE: 26

```
caggtgcaat ggtgcagtc tggggctgag gtgaagaagc ctgggtcctc ggtgaaggtc     60
tcctgcaagg cctccggagg cacattcagc ccctacacta aagctgggt gcgacaggcc    120
```

```
cctggacaag ggctcgagtg gatgggaggg atcgtcccta atgttggtgt agcaacctac    180
gcacagaagt tccagggcag ggtcaccatt actgcagaca atccacgag cacagcctac    240 atggagctga gcagcctgag atctgaggac accgccgtgt attactgtgc gagagatgct    300
gctgataggg actactgggg ccaagggacc accgtgaccg tctcctcagg tggaggcggt    360
tcaggcggag gtggttctgg cggtggcgga tcggatattg ttatgactca atctccactg    420
tctctgccgg tgactccagg cgaaccggcg agcatttctt gccgttccag ccagtctctg    480
ctgcactcca acggctacaa ctatctcgat tggtacctgc aaaaaccggg tcagagccct    540
cagctgctga tctacctggg ctctaaccgc gcttccggtg taccggaccg tttcagcggc    600
tctggatccg gcaccgattt cacgttgaaa atcagccgtg ttgaagcaga agacgtgggc    660
gtttattact gtcagcagcg taataataag aatcgtactt ttggtcaagg caccaaggtc    720
gaaattaaac gt                                                       732
```

<210> SEQ ID NO 27
<211> LENGTH: 244
<212> TYPE: PRT
<213> ORGANISM: Artificial sequence
<220> FEATURE:
<223> OTHER INFORMATION: 8E3 scFv
<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Asp Arg Asp Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Pro Leu Ser Leu Pro Val
    130                 135                 140

Thr Pro Gly Glu Pro Ala Ser Ile Ser Cys Arg Ser Ser Gln Ser Leu
145                 150                 155                 160

Leu His Ser Asn Gly Phe Asn His Leu Tyr Trp Tyr Leu Gln Lys Pro
                165                 170                 175

Gly Gln Ser Pro Gln Leu Leu Ile Tyr Val Gly Gly Asn Arg Ala Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Val Tyr Tyr Cys
    210                 215                 220

Gln Gln Arg Asn Asn Lys Asn Arg Thr Phe Gly Gln Gly Thr Lys Val
225                 230                 235                 240

Glu Ile Lys Arg
```

<210> SEQ ID NO 28
<211> LENGTH: 732
<212> TYPE: DNA
<213> ORGANISM: Artificial sequence
<220> FEATURE:
<223> OTHER INFORMATION: 8E3 scFv

<400> SEQUENCE: 28

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatccta tctttggtac agcaaactac       180
gcacagaagt tccagggcag ggtcaccatt actgcagaca atccacgag cacagcctac      240
atggagctga gcagcctgag atctgaggac accgccgtgt attactgtgc gagagatgct    300
gctgataggg actactgggg ccaagggacc accgtgaccg tctcctcagg tggaggcggt    360
tcaggcggag gtggttctgg cggtggcgga tcggatattg ttatgactca atctccactg    420
tctctgccgg tgactccagg cgaaccggcg agcatttctt gccgttccag ccagtctctg    480
cttcacccca acggcttcaa ccatctctat tggtacctgc aaaaaccggg tcagagccct    540
cagctgctga tctacgtggg gggtaaccgc gcttccggtg taccgaccg tttcagcggc     600
tctggatccg gcaccgattt cacgttgaaa atcagccgtg ttgaagcaga agacgtgggc    660
gtttattact gtcagcagcg taataataag aatcgtactt ttggtcaagg caccaaggtc    720
gaaattaaac gt                                                         732
```

<210> SEQ ID NO 29
<211> LENGTH: 2341
<212> TYPE: DNA
<213> ORGANISM: Artificial sequence
<220> FEATURE:
<223> OTHER INFORMATION: HuFAP alpha-flag

<400> SEQUENCE: 29

```
acgcgtccta gcgctaccgg tcgccaccat gaagacttgg gtaaaatcg tatttggagt      60
tgccacctct gctgtgcttg ccttattggt gatgtgcatt gtcttacgcc ttcaagagt     120
tcataactct gaagaaaata caatgagagc actcacactg aaggatattt taatggaac    180
attttcttat aaaacatttt ttccaaactg gatttcagga caagaatatc ttcatcaatc    240
tgcagataac aatatagtac tttataatat tgaaacagga caatcatata ccattttgag    300
taatagaacc atgaaaagtg tgaatgcttc aaattacggc ttatcacctg atcggcaatt    360
tgtatatcta gaaagtgatt attcaaagct tggagatac tcttacacag caacatatta    420
catctatgac cttagcaatg gagaatttgt aagaggaaat gagcttcctc gtccaattca    480
gtatttatgc tggtcgcctg ttgggagtaa attagcatat gtctatcaaa acaatatcta    540
tttgaaacaa agaccaggag atccacctt tcaaataaca tttaatggaa gagaaaataa    600
aatatttaat ggaatcccag actgggttta tgaagaggaa atgcttgcta caaaatatgc    660
tctctggtgg tctcctaatg aaaattttt ggcatatgcg gaatttaatg atacggatat    720
accagtttatt gcctattcct attatggcga tgaacaatat cctagaacaa taaatattcc    780
atcccaaag gctggagcta agaatcccgt tgttcggata tttattatcg ataccactta    840
ccctgcgtat gtaggtcccc aggaagtgcc tgttccagca atgatagcct caagtgatta    900
ttatttcagt tggctcacgt gggttactga tgaacgagta tgtttgcagt ggctaaaaag    960
agtccagaat gtttcggtcc tgtctatatg tgacttcagg gaagactggc agacatggga  1020
```

```
ttgtccaaag acccaggagc atatagaaga aagcagaact ggatgggctg gtggattctt      1080
tgtttcaaca ccagttttca gctatgatgc catttcgtac tacaaaatat ttagtgacaa      1140
ggatggctac aaacatattc actatatcaa agacactgtg gaaatgcta ttcaaattac       1200 aagtggcaag tgggaggcca taaatatatt cagagtaaca caggattcac tgttttattc      1260
tagcaatgaa tttgaagaat accctggaag aagaaacatc tacagaatta gcattggaag      1320
ctatcctcca agcaagaagt gtgttacttg ccatctaagg aaagaaaggt gccaatatta      1380
cacagcaagt ttcagcgact acgccaagta ctatgcactt gtctgctacg gcccaggcat      1440
ccccatttcc acccttcatg atggacgcac tgatcaagaa attaaatcc tggaagaaaa       1500 caaggaattg gaaaatgctt tgaaaaatat ccagctgcct aaagaggaaa ttaagaaact      1560
tgaagtagat gaaattactt tatggtacaa atgattctt cctcctcaat ttgacagatc        1620
aaagaagtat cccttgctaa ttcaagtgta tggtggtccc tgcagtcaga gtgtaaggtc      1680
tgtatttgct gttaattgga tatcttatct tgcaagtaag gaagggatgg tcattgcctt      1740
ggtggatggt cgaggaacag ctttccaagg tgacaaactc ctctatgcag tgtatcgaaa      1800
gctgggtgtt tatgaagttg aagaccagat tacagctgtc agaaaattca tagaaatggg      1860
tttcattgat gaaaaagaa tagccatatg gggctggtcc tatggaggat acgtttcatc       1920
actgcccctt gcatctggaa ctggtctttt caaatgtggt atagcagtgg ctccagtctc      1980
cagctgggaa tattacgcgt ctgtctacac agagagattc atgggtctcc caacaaagga      2040
tgataatctt gagcactata agaattcaac tgtgatggca agagcagaat atttcagaaa      2100
tgtagactat cttctcatcc acggaacagc agatgataat gtgcactttc aaaactcagc      2160
acagattgct aaagctctgg ttaatgcaca agtggatttc caggcaatgt ggtactctga      2220
ccagaaccac ggcttatccg gcctgtccac gaaccactta tacacccaca tgacccactt      2280
cctaaagcag tgtttctctt tgtcagacga ttacaaagac gatgacgaca gtaagtcga      2340
c                                                                      2341

<210> SEQ ID NO 30
<211> LENGTH: 2344
<212> TYPE: DNA
<213> ORGANISM: Artificial sequence
<220> FEATURE:
<223> OTHER INFORMATION: mFAP-flag

<400> SEQUENCE: 30
acgcgtccta gcgctaccgg tcgccaccat gaagacatgg ctgaaaactg tctttggagt        60
taccaccctg gctgcgcttg ctttagtggt gatatgcatt gtcttacgtc cctcaagagt       120
ttacaaacct gaaggaaaca caaagagagc tcttaccttg aaggatattt taaatggaac       180
attctcatat aaaacatatt ttcccaactg gatttcagaa caagaatatc ttcatcaatc      240
tgaggatgat aacatagtat tttataatat tgaaacaaga gaatcatata tcattttgag      300
taatagcacc atgaaaagtg tgaatgctac agattatggt ttgtcacctg atcggcaatt      360
tgtgtatcta gaaagtgatt attcaaagct ctggcgatat tcatacacag cgacatacta      420
catctacgac cttcagaatg ggaatttgt aagaggatac gagctccctc gtccaattca      480
gtatctatgc tggtcgcctg ttgggagtaa attagcatat gtatatcaaa acaatattta      540
tttgaaacaa agaccaggag atccaccttt tcaaataact tatactggaa gagaaaatag      600
aatatttaat ggaataccag actgggttta tgaagaggaa atgcttgcca caaaatatgc      660
```

-continued

```
tctttggtgg tctccagatg gaaaattttt ggcatatgta gaatttaatg attcagatat    720
accaattatt gcctattctt attatggtga tggacagtat cctagaacta taaatattcc    780
atatccaaag gctggggcta agaatccggt tgttcgtgtt tttattgttg acaccaccta    840
ccctcaccac gtgggcccaa tggaagtgcc agttccagaa atgatagcct caagtgacta    900
ttatttcagc tggctcacat gggtgtccag tgaacgagta tgcttgcagt ggctaaaaag    960
agtgcagaat gtctcagtcc tgtctatatg tgatttcagg gaagactggc atgcatggga   1020
atgtccaaag aaccaggagc atgtagaaga aagcagaaca ggatgggctg gtggattctt   1080
tgtttcgaca ccagctttta gccaggatgc cacttcttac tacaaaatat ttagcgacaa   1140
ggatggttac aaacatattc actacatcaa agacactgtg gaaaatgcta ttcaaattac   1200
aagtggcaag tgggaggcca tatatatatt ccgcgtaaca caggattcac tgttttattc   1260
tagcaatgaa tttgaaggtt accctggaag aagaaacatc tacagaatta gcattggaaa   1320
ctctcctccg agcaagaagt gtgttacttg ccatctaagg aaagaaaggt gccaatatta   1380
cacagcaagt ttcagctaca aagccaagta ctatgcactc gtctgctatg ccctggcct    1440
ccccatttcc accctccatg atggccgcac agaccaagaa atacaagtat tagaagaaaa   1500
caaagaactg gaaaattctc tgagaaatat ccagctgcct aaagtggaga ttaagaagct   1560
caaagacggg ggactgactt tctggtacaa gatgattctg cctcctcagt ttgacagatc   1620
aaagaagtac cctttgctaa ttcaagtgta tggtggtcct tgcagccaga gtgttaagtc   1680
tgtgtttgct gttaattgga taacttatct cgcaagtaag gaggggatag tcattgccct   1740
ggtagatggt cggggcactg ctttccaagg tgacaaattc ctgcatgccg tgtatcgaaa   1800
actgggtgta tatgaagttg aggaccagct cacagctgtc agaaaattca tagaaatggg   1860
tttcattgat gaagaaagaa tagccatatg gggctggtcc tacggaggtt atgtttcatc   1920
cctggcccct gcatctggaa ctggtctttt caaatgtggc atagcagtgg ctccagtctc   1980
cagctgggaa tattacgcat ctatctactc agagagattc atgggcctcc caacaaagga   2040
cgacaatctc gaacactata aaaattcaac tgtgatggca agagcagaat atttcagaaa   2100
tgtagactat cttctcatcc acggaacagc agatgataat gtgcactttc agaactcagc   2160
acagattgct aaagctttgg ttaatgcaca agtggatttc caggcgatgt ggtactctga   2220
ccagaaccat ggtatatcat ctgggcgctc ccagaatcat ttatataccc acatgacgca   2280
cttcctcaag caatgctttt ctttatcaga cgattacaaa gacgatgacg acaagtgagt   2340
cgac                                                               2344
```

<210> SEQ ID NO 31
<211> LENGTH: 21
<212> TYPE: PRT
<213> ORGANISM: Artificial sequence
<220> FEATURE:
<223> OTHER INFORMATION: CD8 alpha signal peptide

<400> SEQUENCE: 31

Met Ala Leu Pro Val Thr Ala Leu Leu Leu Pro Leu Ala Leu Leu Leu
1               5                   10                  15

His Ala Ala Arg Pro
            20

<210> SEQ ID NO 32
<211> LENGTH: 63
<212> TYPE: DNA
<213> ORGANISM: Artificial sequence

```
<220> FEATURE:
<223> OTHER INFORMATION: CD8 alpha signal peptide

<400> SEQUENCE: 32
atggccttac cagtgaccgc cttgctcctg ccgctggcct tgctgctcca cgccgccagg     60
ccg                                                                  63

<210> SEQ ID NO 33
<211> LENGTH: 45
<212> TYPE: PRT
<213> ORGANISM: Artificial sequence
<220> FEATURE:
<223> OTHER INFORMATION: CD8 hinge

<400> SEQUENCE: 33

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 34
<211> LENGTH: 135
<212> TYPE: DNA
<213> ORGANISM: Artificial sequence
<220> FEATURE:
<223> OTHER INFORMATION: CD8 hinge

<400> SEQUENCE: 34
accacgacgc cagcgccgcg accaccaaca ccggcgccca ccatcgcgtc gcagcccctg     60
tccctgcgcc cagaggcgtg ccggccagcg gcggggggcg cagtgcacac gagggggctg    120
gacttcgcct gtgat                                                    135

<210> SEQ ID NO 35
<211> LENGTH: 27
<212> TYPE: PRT
<213> ORGANISM: Artificial sequence
<220> FEATURE:
<223> OTHER INFORMATION: CD28 transmembrane domain

<400> SEQUENCE: 35

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 36
<211> LENGTH: 81
<212> TYPE: DNA
<213> ORGANISM: Artificial sequence
<220> FEATURE:
<223> OTHER INFORMATION: CD28 transmembrane domain

<400> SEQUENCE: 36
ttttgggtgc tggtggtggt tggtggagtc ctggcttgct atagcttgct agtaacagtg     60
gcctttatta ttttctgggt g                                              81

<210> SEQ ID NO 37
<211> LENGTH: 41
<212> TYPE: PRT
<213> ORGANISM: Artificial sequence
```

<220> FEATURE:
<223> OTHER INFORMATION: CD28 intracellular domain

<400> SEQUENCE: 37

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 38
<211> LENGTH: 123
<212> TYPE: DNA
<213> ORGANISM: Artificial sequence
<220> FEATURE:
<223> OTHER INFORMATION: CD28 intracellular domain

<400> SEQUENCE: 38
aggagtaaga ggagcaggct cctgcacagt gactacatga acatgactcc ccgccgcccc      60
gggccaaccc gcaagcatta ccagccctat gccccaccac gcgacttcgc agcctatcgc     120
tcc                                                                    123

<210> SEQ ID NO 39
<211> LENGTH: 113
<212> TYPE: PRT
<213> ORGANISM: Artificial sequence
<220> FEATURE:
<223> OTHER INFORMATION: CD3Z domain

<400> SEQUENCE: 39

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 40
<211> LENGTH: 339
<212> TYPE: DNA
<213> ORGANISM: Artificial sequence
<220> FEATURE:
<223> OTHER INFORMATION: CD3Z domain

<400> SEQUENCE: 40
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgcag agaaggaaga accctcagga aggcctgtac     180

```
aatgaactgc agaaagataa gatggcggag gcctacagtg agattgggat gaaaggcgag    240
cgccggaggg gcaaggggca cgatggcctt taccagggtc tcagtacagc caccaaggac    300
acctacgacg cccttcacat gcaggccctg ccccctcgc                           339
```

```
<210> SEQ ID NO 41
<211> LENGTH: 26
<212> TYPE: DNA
<213> ORGANISM: Artificial sequence
<220> FEATURE:
<223> OTHER INFORMATION: primer

<400> SEQUENCE: 41
caggaaacag ctatgaccat gattac                                         26

<210> SEQ ID NO 42
<211> LENGTH: 75
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (37)..(38)
<223> OTHER INFORMATION: n is a, c, g or t
<220> FEATURE:
<221> NAME/KEY: misc_feature
<222> LOCATION: (40)..(41)
<223> OTHER INFORMATION: n is a, c, g or t
<220> FEATURE:
<221> NAME/KEY: misc_feature
<222> LOCATION: (43)..(44)
<223> OTHER INFORMATION: n is a, c, g or t
<220> FEATURE:
<221> NAME/KEY: misc_feature
<222> LOCATION: (46)..(47)
<223> OTHER INFORMATION: n is a, c, g or t
<220> FEATURE:
<221> NAME/KEY: misc_feature
<222> LOCATION: (49)..(50)
<223> OTHER INFORMATION: n is a, c, g or t
<220> FEATURE:
<221> NAME/KEY: misc_feature
<222> LOCATION: (52)..(53)
<223> OTHER INFORMATION: n is a, c, g or t

<400> SEQUENCE: 42
cactcgagcc cttgtccagg ggcctgtcgc acccamnnmn nmnnmnnmnn mnngaatgtg    60
cctccggagg ccttg                                                     75

<210> SEQ ID NO 43
<211> LENGTH: 80
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g or t
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (40)..(41)
<223> OTHER INFORMATION: n is a, c, g or t
<220> FEATURE:
<221> NAME/KEY: misc_feature
<222> LOCATION: (43)..(44)
<223> OTHER INFORMATION: n is a, c, g or t
```

```
<220> FEATURE:
<221> NAME/KEY: misc_feature
<222> LOCATION: (49)..(50)
<223> OTHER INFORMATION: n is a, c, g or t
<220> FEATURE:
<221> NAME/KEY: misc_feature
<222> LOCATION: (55)..(56)
<223> OTHER INFORMATION: n is a, c, g or t

<400> SEQUENCE: 43
cctggacaag ggctcgagtg gatgggannk atcnnkcctn nknnkggtnn kgcannktac      60
gcacagaagt tccagggcag                                                 80

<210> SEQ ID NO 44
<211> LENGTH: 30
<212> TYPE: DNA
<213> ORGANISM: Artificial sequence
<220> FEATURE:
<223> OTHER INFORMATION: primer

<400> SEQUENCE: 44
gacgttagta aatgaatttt ctgtatgagg                                      30

<210> SEQ ID NO 45
<211> LENGTH: 89
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (38)..(39)
<223> OTHER INFORMATION: n is a, c, g or t
<220> FEATURE:
<221> NAME/KEY: misc_feature
<222> LOCATION: (44)..(45)
<223> OTHER INFORMATION: n is a, c, g or t
<220> FEATURE:
<221> NAME/KEY: misc_feature
<222> LOCATION: (47)..(48)
<223> OTHER INFORMATION: n is a, c, g or t
<220> FEATURE:
<221> NAME/KEY: misc_feature
<222> LOCATION: (50)..(51)
<223> OTHER INFORMATION: n is a, c, g or t
<220> FEATURE:
<221> NAME/KEY: misc_feature
<222> LOCATION: (56)..(57)
<223> OTHER INFORMATION: n is a, c, g or t
<220> FEATURE:
<221> NAME/KEY: misc_feature
<222> LOCATION: (59)..(60)
<223> OTHER INFORMATION: n is a, c, g or t
<220> FEATURE:
<221> NAME/KEY: misc_feature
<222> LOCATION: (62)..(63)
<223> OTHER INFORMATION: n is a, c, g or t
<220> FEATURE:
<221> NAME/KEY: misc_feature
<222> LOCATION: (65)..(66)
<223> OTHER INFORMATION: n is a, c, g or t

<400> SEQUENCE: 45
cagctgaggg ctctgacccg gttttttgcag gtaccamnng agmnnmnnmn ngccmnnmnn    60
mnnmnncaga gactggctgg aacggcaag                                       89

<210> SEQ ID NO 46
<211> LENGTH: 68
<212> TYPE: DNA
<213> ORGANISM: Artificial sequence
<220> FEATURE:
```

```
<223> OTHER INFORMATION: primer
<220> FEATURE:
<221> NAME/KEY: misc_feature
<222> LOCATION: (27)..(28)
<223> OTHER INFORMATION: n is a, c, g or t
<220> FEATURE:
<221> NAME/KEY: misc_feature
<222> LOCATION: (30)..(31)
<223> OTHER INFORMATION: n is a, c, g or t
<220> FEATURE:
<221> NAME/KEY: misc_feature
<222> LOCATION: (33)..(34)
<223> OTHER INFORMATION: n is a, c, g or t
<220> FEATURE:
<221> NAME/KEY: misc_feature
<222> LOCATION: (36)..(37)
<223> OTHER INFORMATION: n is a, c, g or t
<220> FEATURE:
<221> NAME/KEY: misc_feature
<222> LOCATION: (39)..(40)
<223> OTHER INFORMATION: n is a, c, g or t

<400> SEQUENCE: 46
cgggtcagag ccctcagctg ctgatcnnkn nknnknnknn kcgcgcttcc ggtgtaccgg    60
accgtttc                                                            68

<210> SEQ ID NO 47
<211> LENGTH: 42
<212> TYPE: PRT
<213> ORGANISM: Artificial sequence
<220> FEATURE:
<223> OTHER INFORMATION: CD137 intracellular domain

<400> SEQUENCE: 47

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 48
<211> LENGTH: 470
<212> TYPE: PRT
<213> ORGANISM: Artificial sequence
<220> FEATURE:
<223> OTHER INFORMATION: 8E3-28Z

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Asp Arg Asp Tyr Trp Gly Gln Gly Thr Thr Val
            100                 105                 110

Thr Val Ser Ser Gly Gly Gly Gly Ser Gly Gly Gly Gly Ser Gly Gly
```

-continued

```
                115                 120                 125
Gly Gly Ser Asp Ile Val Met Thr Gln Ser Pro Leu Ser Leu Pro Val
            130                 135                 140

Thr Pro Gly Glu Pro Ala Ser Ile Ser Cys Arg Ser Ser Gln Ser Leu
145                 150                 155                 160

Leu His Pro Asn Gly Phe Asn His Leu Tyr Trp Tyr Leu Gln Lys Pro
                165                 170                 175

Gly Gln Ser Pro Gln Leu Leu Ile Tyr Val Gly Gly Asn Arg Ala Ser
            180                 185                 190

Gly Val Pro Asp Arg Phe Ser Gly Ser Gly Ser Gly Thr Asp Phe Thr
            195                 200                 205

Leu Lys Ile Ser Arg Val Glu Ala Glu Asp Val Gly Val Tyr Tyr Cys
        210                 215                 220

Gln Gln Arg Asn Asn Lys Asn Arg Thr Phe Gly Gln Gly Thr Lys Val
225                 230                 235                 240

Glu Ile Lys Arg Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
                260                 265                 270

Pro Ala Ala Gly Gly Ala Val His Thr Arg Gly Leu Asp Phe Ala Cys
            275                 280                 285

Asp Phe Trp Val Leu Val Val Val Gly Gly Val Leu Ala Cys Tyr Ser
        290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

Gly Pro Thr Arg Lys His Tyr Gln Pro Tyr Ala Pro Pro Arg Asp Phe
                340                 345                 350

Ala Ala Tyr Arg Ser Arg Val Lys Phe Ser Arg Ser Ala Asp Ala Pro
            355                 360                 365

Ala Tyr Gln Gln Gly Gln Asn Gln Leu Tyr Asn Glu Leu Asn Leu Gly
        370                 375                 380

Arg Arg Glu Glu Tyr Asp Val Leu Asp Lys Arg Arg Gly Arg Asp Pro
385                 390                 395                 400

Glu Met Gly Gly Lys Pro Gln Arg Arg Lys Asn Pro Gln Glu Gly Leu
                405                 410                 415

Tyr Asn Glu Leu Gln Lys Asp Lys Met Ala Glu Ala Tyr Ser Glu Ile
                420                 425                 430

Gly Met Lys Gly Glu Arg Arg Arg Gly Lys Gly His Asp Gly Leu Tyr
            435                 440                 445

Gln Gly Leu Ser Thr Ala Thr Lys Asp Thr Tyr Asp Ala Leu His Met
        450                 455                 460

Gln Ala Leu Pro Pro Arg
465                 470
```

BINDING UNIT TARGETING FIBROBLAST ACTIVATION PROTEIN α AND APPLICATION THEREOF

TECHNICAL FIELD

The present invention relates to the field of biomedicine; and in particular, the present invention relates to a binding unit that specifically binds to FAPα, a polynucleotide encoding such binding unit, a vector and a host cell containing such polynucleotide. The present invention also relates to a method for generating the antigen binding unit and a method for using it for treating diseases.

BACKGROUND

Fibroblast activation protein a (FAPα) is an antigen molecule (NCBI Reference Sequence: NP_001278736.1) specifically expressed on the surface of tumor-associated fibroblasts (CAF), which belongs to the serine protease family, possesses activities of collagenase and dipeptidyl peptidase, play an important role in the degradation and reconstruction of the tumor-host interface matrix, and participate in the growth, invasion and metastasis of tumor. FAPα is selectively expressed in the matrix of more than 90% of malignant epithelial tumors (such as breast cancer, ovarian cancer, lung cancer, colon cancer, pancreatic cancer, skin melanoma, kidney cancer, bladder cancer, etc.), embryonic tissues, healing wounds and physiologically reconstructed organs, but is not normally expressed in normal adult tissues, which make FAPα an antigen target for imaging, diagnosis and treatment of various tumors.

Human FAPα was initially identified in cultured fibroblasts using monoclonal antibody (mAb) F19 (described in WO93/05804, ATCC number HB8269). Based on the humanization of the F19 antibody, Sibrotuzumab/BIBH1 was developed. Phase I study using Sirolizumab demonstrated the specific accumulation of $131^I$ labeled antibodies in a tumor (Scott et al. Clin Cancer Res 9, 1639-1647 (2003)). However, an early phase II trial of unconjugated sirolimumab in patients with metastatic colorectal cancer was stopped due to the lack of efficacy to inhibit tumor development (Hofheinz et al., Inkologie 26, 44-48 (2003)).

Therefore, there is still a need in the art for enhanced therapies, including antibodies targeting FaPα with improved efficacy for treating cancer.

SUMMARY OF THE INVENTION

The purpose of the present invention is to find binding units that specifically bind to FaPα, including but not limited to antibodies and to develop immune effector cells targeting FaPα.

In a first aspect, the present invention provides an antigen binding unit comprising a light chain CDR region and a heavy chain CDR region, the heavy chain CDR comprises HCDR1, HCDR2 and HCDR3, and the light chain CDR region comprises LCDR1, LCDR2 and LCDR3;
wherein the sequences of the HCDR1, HCDR2 and HCDR3 are independently selected from the group consisting of SEQ ID NO: 1-3, 7 and 8, and the sequences of the LCDR1, LCDR2 and LCDR3 are independently selected from the group consisting of SEQ ID NO: 4-6, 9 and 10.

In a specific embodiment, the HCDR1 has the sequence as shown in SEQ ID NO: 1 or 7, the HCDR2 has the sequence as shown in SEQ ID NO: 2 or 8, and the HCDR3 has the sequence as shown in SEQ ID NO: 3.

In a specific embodiment, the sequences of HCDR1, HCDR2 and HCDR3 are selected from any one of the following groups:
A. SEQ ID NO: 1, SEQ ID NO: 2, SEQ ID NO: 3;
B. SEQ ID NO: 7, SEQ ID NO: 8, SEQ ID NO: 3.

In a specific embodiment, the LCDR1 has the sequence as shown in SEQ ID NO: 4 or 9, the LCDR2 has the sequence as shown in SEQ ID NO: 5 or 10, and the LCDR3 has the sequence as shown in SEQ ID NO: 6.

In a specific embodiment, the sequences of LCDR1, LCDR2, and LCDR3 are selected from any one of the following groups:
A. SEQ ID NO: 4, SEQ ID NO: 5, SEQ ID NO: 6;
B. SEQ ID NO: 9, SEQ ID NO: 10, SEQ ID NO: 6.

In a specific embodiment, the HCDR1 has the sequence as shown in SEQ ID NO: 1 or 7, the HCDR2 has the sequence as shown in SEQ ID NO: 2 or 8, the HCDR3 has the sequence as shown in SEQ ID NO: 3, the LCDR1 has the sequence as shown in SEQ ID NO: 4 or 9, the LCDR2 has the sequence as shown in SEQ ID NO: 5 or 10, and the LCDR3 has the sequence as shown in SEQ ID NO: 6.

In a specific embodiment, the HCDR1 comprises the sequence as shown in SEQ ID NO: 1, the HCDR2 comprises the sequence as shown in SEQ ID NO: 2, and the HCDR3 comprises the sequence as shown in SEQ ID NO: 3, the LCDR1 comprises the sequence as shown in SEQ ID NO: 4, the LCDR2 comprises the sequence as shown in SEQ ID NO: 5, and the LCDR3 comprises the sequence as shown in SEQ ID NO: 6; or The HCDR1 comprises the sequence as shown in SEQ ID NO: 7, the HCDR2 comprises the sequence as shown in SEQ ID NO: 8, the HCDR3 comprises the sequence as shown in SEQ ID NO: 3, the LCDR1 comprises the sequence as shown in SEQ ID NO: 4, the LCDR2 comprises the sequence as shown in SEQ ID NO: 5, and the LCDR3 comprises the sequence as shown in SEQ ID NO: 6; or The HCDR1 comprises the sequence as shown in SEQ ID NO: 1, the HCDR2 comprises the sequence as shown in SEQ ID NO: 2, the HCDR3 comprises the sequence as shown in SEQ ID NO: 3, the LCDR1 comprises the sequence as shown in SEQ ID NO: 9, the LCDR2 comprises the sequence as shown in SEQ ID NO: 10, and the LCDR3 comprises the sequence as shown in SEQ ID NO: 6.

In a specific embodiment, the antigen binding unit has a heavy chain variable region as shown in SEQ ID NO: 11 or 15, and a light chain variable region as shown in SEQ ID NO: 13 or 17.

In a preferred embodiment, the antigen binding unit is an antibody, preferably a monoclonal antibody or an active fragment thereof.

In a second aspect, the present invention provides a mutant of the antigen binding unit of the first aspect, which competes with the antigen binding unit of the first aspect for binding to FAPα.

In a specific embodiment, the light chain variable region sequence of the mutant has 90%, 91%, 92%, 93%, 94%, 95%, 96%, 97%, 98% or 99% identity with that of the antigen-binding unit of the first aspect; or, the heavy chain variable region sequence of the mutant has 90%, 91%, 92%, 93%, 94%, 95%, 96%, 97%, 98% or 99% identity with that of the antigen-binding unit of any one of claims 1-8;

Preferably, the sequence of the light chain CDR region of the mutant, such as the light chain CDR1 or CDR2 has more than 70%; preferably, more than 75%; more preferably, more than 80% identity with that of the antigen binding unit according to the first aspect; or, the sequence of the heavy chain CDR region of the mutant, such as the heavy chain CDR1 or CDR2 has more than 70%; preferably, more than 75%; more preferably, more than 80% identity with that of the antigen binding unit according to the first aspect.

In a specific embodiment, the mutant competes with the antigen binding unit according to the first aspect for binding to the same binding epitope on FAPα.

In a third aspect, the present invention provides an antigen binding unit comprising a light chain CDR region and a heavy chain CDR region, the heavy chain CDR comprises HCDR1, HCDR2 and HCDR3, and the light chain CDR region comprises LCDR1, LCDR2 and LCDR3, wherein the HCDR1, HCDR2 and HCDR3 are independently selected from a sequence having at least 80%, preferably at least 85%, more preferably at least 90%, more preferably at least 91%, 92%, 93%, 94%, 95%, 96%, 97%, 98% or 99% similarity with any sequence of SEQ ID NO: 1-3, 7 and 8, and the LCDR1, LCDR2 and LCDR3 are independently selected from a sequence having at least 80%, preferably at least 85%, more preferably at least 90%, more preferably at least 91%, 92%, 93%, 94%, 95%, 96%, 97%, 98% or 99% similarity with any sequence of SEQ ID NO: 4-6, 9 and 10.

In a specific embodiment, the HCDR1 has the sequence as shown in SEQ ID NO: 1 or 7, the HCDR2 has the sequence as shown in SEQ ID NO: 2 or 8, and the HCDR3 has the sequence as shown in SEQ ID NO: 3.

In a specific embodiment, the sequences of HCDR1, HCDR2 and HCDR3 are selected from any one of the following groups:
A. SEQ ID NO: 1, SEQ ID NO: 2, SEQ ID NO: 3;
B. SEQ ID NO: 7, SEQ ID NO: 8, SEQ ID NO: 3.

In a specific embodiment, the LCDR1 has the sequence as shown in SEQ ID NO: 4 or 9, the LCDR2 has the sequence as shown in SEQ ID NO: 5 or 10, and the LCDR3 has the sequence as shown in SEQ ID NO: 6.

In a specific embodiment, the sequences of LCDR1, LCDR2, and LCDR3 are selected from any one of the following groups:
A. SEQ ID NO: 4, SEQ ID NO: 5, SEQ ID NO: 6;
B. SEQ ID NO: 9, SEQ ID NO: 10, SEQ ID NO: 6.

In a specific embodiment, the HCDR1 has the sequence as shown in SEQ ID NO: 1 or 7, the HCDR2 has the sequence as shown in SEQ ID NO: 2 or 8, the HCDR3 has the sequence as shown in SEQ ID NO: 3, the LCDR1 has the sequence as shown in SEQ ID NO: 4 or 9, the LCDR2 has the sequence as shown in SEQ ID NO: 5 or 10, and the LCDR3 has the sequence as shown in SEQ ID NO: 6.

In a specific embodiment, the HCDR1 comprises the sequence as shown in SEQ ID NO: 1, the HCDR2 comprises the sequence as shown in SEQ ID NO: 2, the HCDR3 comprises the sequence as shown in SEQ ID NO: 3, the LCDR1 comprises the sequence as shown in SEQ ID NO: 4, the LCDR2 comprises the sequence as shown in SEQ ID NO: 5, and the LCDR3 comprises the sequence as shown in SEQ ID NO: 6; or The HCDR1 comprises the sequence as shown in SEQ ID NO: 7, the HCDR2 comprises the sequence as shown in SEQ ID NO: 8, the HCDR3 comprises the sequence as shown in SEQ ID NO: 3, the LCDR1 comprises the sequence as shown in SEQ ID NO: 4, the LCDR2 comprises the sequence as shown in SEQ ID NO: 5, and the LCDR3 comprises the sequence as shown in SEQ ID NO: 6; or The HCDR1 comprises the sequence as shown in SEQ ID NO: 1, the HCDR2 comprises the sequence as shown in SEQ ID NO: 2, the HCDR3 comprises the sequence as shown in SEQ ID NO: 3, the LCDR1 comprises the sequence as shown in SEQ ID NO: 9, the LCDR2 comprises the sequence as shown in SEQ ID NO: 10, and the LCDR3 comprises the sequence as shown in SEQ ID NO: 6.

In a fourth aspect, the present invention provides an antigen binding unit, wherein the antigen binding unit has a sequence having at least 80%, preferably at least 85%, more preferably at least 90%, more preferably at least 91%, 92%, 93%, 94%, 95%, 96%, 97%, 98% or 99% similarity with the sequence of the heavy chain variable region as shown in SEQ ID NO: 11 or 15 and a sequence having at least 80%, preferably at least 85%, more preferably at least 90%, more preferably at least 91%, 92%, 93%, 94%, 95%, 96%, 97%, 98% or 99% similarity with the light chain variable region as shown in SEQ ID NO: 13 or 17.

In a fifth aspect, the present invention provides the antigen binding unit or the mutant if the antigen binding unit according to the first to fourth aspects, wherein the antigen binding unit is a monoclonal antibody, a fully human antibody, a humanized antibody, a chimeric antibody.

In a specific embodiment, the antigen binding unit is scFv, Fv, Fab, (Fab)$_2$ or single domain antibody.

In a sixth aspect, the present invention provides a nucleic acid encoding the antigen binding unit according to the first to fifth aspects.

In a seventh aspect, the present invention provides an expression vector comprising the nucleic acid of the sixth aspect.

In an eighth aspect, the present invention provides a host cell comprising the expression vector of the seventh aspect or having the nucleic acid of the sixth aspect integrated into its genome.

In a ninth aspect, the present invention provides a bivalent protein, which is an antibody having a human immunoglobulin Fc region formed by fusing the scFv sequence of the fifth aspect with one or more heavy chain constant regions;

Preferably, the human immunoglobulin Fc region is connected with a conjugate; preferably, the conjugate is selected from a fluorescent dye, cytotoxin, or radioisotope.

In a tenth aspect, the present invention provides a multifunctional immunoconjugate. The multifunctional immunoconjugate includes:

The antigen binding unit according to the first to fifth aspects, and a functional molecule connected thereto; wherein the functional molecule is selected from:

(a) molecules targeting tumor surface markers, including antibodies or ligands that bind to immune cell surface markers; and preferably, the immune cell surface markers include: CD3, CD16, CD28; more preferably, the antibody that binds to the immune cell surface marker is an anti-CD3 antibody; and most preferably, the molecule targeting the immune cell surface marker is an antibody that binds to the surface marker of T cells;

(b) tumor-inhibiting molecules, including anti-tumor cytokines or anti-tumor toxins, and preferably, the cytokines include: IL-12, IL-15, type I interferon, TNF-alpha;

(c) detectable markers or molecules that target immune cell surface markers.

In an eleventh aspect, the present invention provides a chimeric antigen receptor, the extracellular domain of the chimeric antigen receptor comprises the antigen binding unit according to the first to fifth aspects, and the antigen binding unit is preferably a single chain antibody or single domain antibody.

In a preferred embodiment, the chimeric antigen receptor further comprises a transmembrane domain and an intracellular signal domain, the transmembrane domain is preferably selected from: α, β, zeta chain of TCR, transmembrane domain of CD3ε, CD3ζ, CD4, CD5, CD8α, CD9, CD16, CD22, CD27, CD28, CD33, CD37, CD45, CD64, CD80, CD86, CD134, CD137, CD152, CD154, and PD1; more preferably, selected from: transmembrane domain of CD8α, CD4, CD45, PD1, CD154, and CD28;

and/or the intracellular signal domain includes one or more costimulatory signal domains and/or primary signal domains; wherein the costimulatory signal domains are preferably selected from: intracellular signaling regions of CARD11, CD2, CD7, CD27, CD28, CD30, CD40, CD54, CD83, OX40, CD137, CD134, CD150, CD152, CD223, CD270, PD-L2, PD-L1, CD278, DAP10, LAT, NKD2C SLP76, TRIM, FcεRIγ, MyD88, and 41BBL; and/or the primary signal domain is selected from: TCR ζ, FcR γ, FcR β, CD3 γ, CD3δ, CD3ε, CD5, CD22, CD79a, CD79b, CD278 (also nameed as "ICOS") and CD66d, and CD3ζ; and more preferably, selected from: CD137, CD134, CD28 and OX40; and/or the primary signal domain is selected from CD3ζ.

In a preferred embodiment, the transmembrane domain is selected from CD8α or CD28, the costimulatory signal domain is selected from the intracellular signal domain of CD137 or CD28, and the primary signal domain is selected from CD3ζ.

In a specific embodiment, the chimeric antigen receptor includes an antibody, a transmembrane region and an intracellular signal region connected in the following order:

The antigen binding unit of the first to fifth aspects, CD8 and CD3ζ;

The antigen binding unit of the first to fifth aspects, CD8, CD137 and CD3ζ;

The antigen-binding unit of the first to fifth aspects, the transmembrane region of CD28 molecule, the intracellular signal region of CD28 molecule and CD3ζ; or The antigen binding unit of the first to fifth aspects, the transmembrane region of CD28 molecule, the intracellular signal region of CD28 molecule, CD137 and CD3ζ.

In a twelfth aspect, the present invention provides a nucleotide sequence encoding the chimeric antigen receptor of the eleventh aspect.

In a thirteenth aspect, the present invention provides an expression vector, comprising the nucleotide sequence of the twelfth aspect.

In a fourteenth aspect, the present invention provides a virus, comprising the expression vector of the thirteenth aspect.

In a fifteenth aspect, the present invention provides a genetically modified immune cell, which is transduced with the nucleotide sequence of the twelfth aspect, or the expression vector of the thirteenth aspect, or the virus of the fourteenth aspect; or, expresses the chimeric antigen receptor of the eleventh aspect.

In a preferred embodiment, the immune cells include but are not limited to the following cells and combinations thereof: T lymphocytes, NK cells or NKT cells.

In a specific embodiment, the genetically modified immune cells also express other sequences than the chimeric antigen receptor. The other sequences include cytokines, another chimeric antigen receptor, chemokine receptors, siRNA reducing PD-1 expression or a protein blocking PD-L1, TCR, or safety switches;

Preferably, the cytokines include IL-12, IL-15, IL-21, or type I interferon;

Preferably, the chemokine receptor includes CCR2, CCR5, CXCR2, or CXCR4;

Preferably, the safety switch includes iCaspase-9, Truancated EGFR or RQR8.

In a sixteenth aspect, the present invention provides uses of the antigen binding unit of the first to fifth aspects, or the bivalent protein of the ninth aspect, or the immunoconjugate of the tenth aspect, or the chimeric antigen receptor of the eleventh aspect, or the nucleotide sequence of the twelfth aspect, or the expression vector of the thirteenth aspect, or the virus of the fourteenth aspect, or the immune cells of the fifteenth aspect, in the preparation of a medicament or reagent for the treatment, prevention or diagnosis of diseases associated with high expression of FAPα.

In a specific embodiment, the disease associated with high expression of FaPα is a tumor.

In a specific embodiment, the tumor is breast cancer, ovarian cancer, lung cancer, colon cancer, pancreatic cancer, cutaneous melanoma, kidney cancer or bladder cancer.

In a seventeenth aspect, the present invention provides a pharmaceutical composition comprising the antigen binding unit of the first to fifth aspects or the nucleic acid encoding the antigen binding unit; or The bivalent protein of the ninth aspect; or The immunoconjugate of the tenth aspect or a nucleic acid encoding the conjugate; or The chimeric antigen receptor of the eleventh aspect or a nucleic acid encoding the chimeric antigen receptor; or The genetically modified immune cell of the fifteenth aspect.

It should be understood that, within the scope of the present invention, the above technical features of the present invention and the technical features specifically described in the following conents (e.g., Examples) can be combined with each other, thereby forming new or preferred technical solutions, which may not necessarily repeated here.

DESCRIPTION OF DRAWINGS

FIG. 5 shows the sequence alignment (scFv) of antibodies 1A7, 8E3 with the parent antibody 10A4;

MODES FOR CARRYING OUT THE INVENTION

Figure 1:
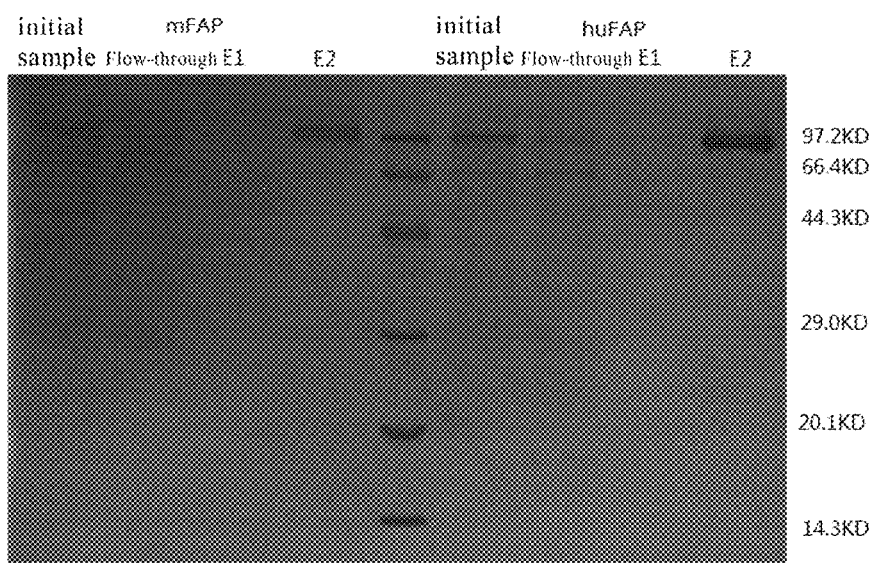
FIG. 1 shows the results of SDS PAGE analysis of recombinant human FAPα_His (huFAP), mouse FAP_His (mFAP) purified by nickel column.

After extensive and in-depth research, the inventor unexpectedly discovered antibodies that specifically bind to FAP, and developed immune effector cells that specifically target FAP based on this antibody. The antibody of the present invention can effectively bind to tumor cells expressing FAP, and the immune effector cells of the present invention exhibit significant killing effects to tumor cells expressing FAP, and thus can be effectively and safely applied to treat malignant tumors such as multiple myeloma. The present invention has been completed based on the above findings.

The following detailed description shows embodiments disclosed herein in detail. It should be understood that this description is not intended to limit the invention to the specific embodiments disclosed herein, which may vary. A skilled person in the art will understand that the contents disclosed in this description may exist many changes or variations, all of which shall fall within the disclosed scope and principles. Unless otherwise stated, each embodiment can be arbitrarily combined with any other embodiment.

Certain embodiments disclosed herein include numerical ranges, and certain aspects of the invention can be described in terms of ranges. Unless otherwise stated, it should be understood that a numerical range or description of a range is provided for brevity and convenience only, and should not be considered as a strict limitation on the scope of the present invention. Therefore, a description of a range should be deemed as that all possible sub-ranges and all possible specific numerical points within the range are specifically disclosed, as if these sub-ranges and numerical points are explicitly written in this text.

When referring to measurable values such as amount, temporary duration, etc., the term "about" means that ±20%, or in some cases ±10%, or in some cases ±5%, or in some cases ±1%, or in some cases ±0.1% of a specified value is included.

Definition on Terms

The terminology used herein has a meaning similar to those conventionally understood by a skilled person in the art. For clarity, some terms are defined below.

As used herein, the term "FAPα" refers to fibroblast activation protein α. Human fibroblast activation protein α is a transmembrane protein composed of 760 amino acid residues (NCBI Reference Sequence: NP_001278736.1). Unless otherwise specified, FAPα herein refers to human fibroblast activation protein α. The mouse fibroblast activation protein consists of 761 amino acid residues (a transmembrane protein consisting of 760 amino acid residues, NCBI Reference Sequence: NP_032012.1).

As used herein, the term "binding unit", "antigen binding unit" or "antigen binding protein" has the same meaning and can be used interchangeably herein to refer to immunoglobulin molecules and any form of immunologically active moieties of immunoglobulin molecules; that is, a molecule comprising an antigen binding site that specifically binds to an antigen or is immunoreactive with an antigen. The simplest naturally-occurring antibody (e.g., IgG) structurally has 4 polypeptide chains, two heavy (H) chains and two light (L) chains connected to each other via disulfide bonds. Immunoglobulins represent a large family of molecules, including several molecular types, such as IgD, IgG, IgA, IgM and IgE. Antigen binding units include, but are not limited to, Fv, scFv, dFv, dAb, two-chain antibody, three-chain antibody, four-chain antibody, domain Ab, Fab fragment, Fab', (Fab')$_2$, bispecific antibody and multispecific antibody.

As used herein, the term "competitive binding" means that two or more substances bind to the same position of a binding target, for example, the same binding epitope of an antigen; in other words, the "competitive binding" does not exist between different substances that bind to different positions on the same binding target.

As used herein, the term "antigen binding unit" also includes immunoglobulin molecules from various species, including invertebrates and vertebrates. The term "human" as applied to the antigen binding unit means that an immunoglobulin molecule is expressed by a human gene or fragments thereof. The term "humanized" as applied to non-human (e.g., rodent or primate) antibodies means that a hybrid immunoglobulin, immunoglobulin chain or fragments thereof comprises minimal sequence derived from non-human immunoglobulin. For the most parts, humanized antibodies are human immunoglobulins (recipient antibodies), in which residues from the complementarity determining region (CDR) of the recipient are replaced by residues of CDR (donor antibody) of non-human species (e.g., mouse, rat, rabbit or primate). In some cases, FAT framework region (FR) residues of a non-human immunoglobulin are replaced by corresponding human residues. In addition, a humanized antibody may comprise residues found neither in the recipient antibody nor in the imported CDR or framework sequences. Such modifications are made to further refine and optimize performance of an antibody and minimize immunogenicity when the antibody is introduced into a human body. In general, a humanized antibody comprises substantially all, at least one and usually two variable domains, wherein all or substantially all CDR regions correspond to CDR regions of a non-human immunoglobulin and all or substantially all FR regions are FR regions of a non-human immunoglobulin sequence.

As a term known in the art, the term "antibody" as used herein refer to an antigen binding protein of the immune system. The term "antibody" as mentioned herein includes a complete full-length antibody having an antigen-binding region and any fragments thereof in which the "antigen-binding portion" or "antigen-binding region" is retained, or single chains thereof such as single chain variable fragments (scFv). A natural antibody refers to a glycoprotein comprising at least two heavy (H) chains and two light (L) chains interconnected via disulfide bonds or antigen-binding fragments. The term "antibody" also includes all recombinant forms of an antibody (particularly the antibodies described herein), such as an antibody expressed in prokaryotic cells, unglycosylated antibody as well as antibody fragments that bind to an antigen and derivatives described below. Each heavy chain is composed of a heavy chain variable region (abbreviated herein as $V_H$) and a heavy chain constant region. Each light chain is composed of a light chain variable region (abbreviated herein as $V_L$) and a light chain constant region. $V_H$ and $V_L$ can be further subdivided into hypervariable regions called complementarity determining regions (CDR), which are interspersed in more conserved regions called framework regions (FR). Each $V_H$ and $V_L$ is composed of three CDRs and four FRs, and is arranged in the following order from the amino end to carboxyl end: FR1, CDR1, FR2, CDR2, FR3, CDR3, FR4. The variable regions of the heavy and light chains contain binding domains that interact with an antigen. The constant region of the antibody can mediate the binding of the immunoglobulin to host tissues or factors, including various cells of the immune system (such as effector cells) and the first component of classical complement system (C1q).

As used herein, the term "Fab'" or "Fab region" includes polypeptides comprising $V_H$, $C_{H1}$, $V_L$ and $C_L$ immunoglobulin domains. Fab may refer to this isolated region, or this region is located in the context of a full-length antibody or antibody fragment.

As used herein, the term "Fc" or "Fc region" includes a polypeptide comprising antibody constant regions other than the immunoglobulin domain of the first constant region. Therefore, Fc refers to the immunoglobulin domain of the last two constant regions of IgA, IgD and IgG, and the immunoglobulin domain of the last three constant regions of IgE and IgM, as well as a flexible hinge at the N-terminus of these domains. For IgA and IgM, Fc may include J chain. For IgG, Fc includes immunoglobulin domains Cγ2 and Cγ3 as well as a hinge between Cγ1 and Cγ2. Although the boundaries of a Fc region may vary, the human IgG heavy chain Fc region is usually defined as comprising residues C226 or P230 at its carboxyl terminus, where the numbering is according to the EU index of Kabat. For human IgG1, Fc is defined herein as comprising residue P232 to its carboxyl terminus, where the numbering is according to the EU index of Kabat. Fc may refer to this isolated region, or this region locates in the environment of an Fc polypeptide, such as an antibody.

As used herein, the term "parent antibody" or "parent immunoglobulin" includes unmodified antibodies, which are then modified to produce variants. The parent antibody may be a naturally occurring antibody, or a variant or engineered version of a naturally occurring antibody. The parent antibody may refer to the antibody itself, a composition comprising the parent antibody, or an encoding amino acid sequence thereof. As used herein, the term "parent antibody" or "parent immunoglobulin" includes murine or chimeric antibodies that are subsequently modified to produce humanized antibodies.

As used herein, the term "variant antibody" or "antibody variant" or "variant" includes an antibody sequence that differ from the parent antibody sequence due to at least one amino acid modification compared with the parent. Antibody variants can refer to the antibody itself or to a composition comprising the parent antibody. In a specific embodiment, the light chain variable region sequence of the variant antibody described herein has 90%, 91%, 92%, 93%, 94%, 95%, 96%, 97%, 98% or 99% identity with the light chain variable region sequence of the parent antibody; the heavy chain variable region sequence of the variant antibody described herein has 90%, 91%, 92%, 93%, 94%, 95%, 96%, 97%, 98% or 99% identity with the heavy chain variable region sequence of the parent antibody. In a preferred embodiment, the sequence of the light chain CDR region of the variant antibody described herein, such as the light chain CDR1 or CDR2, has more than 70% identity; preferably, more than 75% identity; more preferably, more than 80% identity with the sequence of the light chain CDR region of the parent antibody, such as the light chain CDR1 or CDR2; and the sequence of the heavy chain CDR region of the variant antibody described herein, such as the heavy chain CDR1 or CDR2, has more than 60% identity; preferably, more than 70% identity; more preferably, more than 80% identity with the sequence of the heavy chain CDR region of the parent antibody, such as the heavy chain CDR1 or CDR2.

The term "amino acid modification" includes amino acid substitutions, additions and/or deletions, and "amino acid substitution" means that an amino acid at a specific position in the parent polypeptide sequence is replaced with another amino acid. For example, the substitution R94K means that arginine at position 94 is replaced with lysine, and "amino acid insertion" as used herein means that an amino acid is added at a specific position in the parent polypeptide sequence. As used herein, "amino acid deletion" or "deletion" means that an amino acid at a specific position in the parent polypeptide sequence is deleted.

As used herein, the term "conservative modification" or "conservative sequence modification" refers to an amino acid modification that does not significantly affect or change the binding characteristics of an antibody comprising the amino acid sequence. Such conservative modifications include amino acid substitutions, insertions and deletions. Modifications can be introduced into the antibody of the invention by standard techniques known in the art, such as site-directed mutagenesis and PCR-mediated mutagenesis. Conservative amino acid substitutions are substitutions of amino acid residues with amino acid residues having similar side chains. Families of amino acid residues with similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, serine, threonine, tyrosine, cysteine, tryptophan), non-polar side chains (e.g., alanine, valine, leucine, isole Amino acid, proline, phenylalanine, methionine), β branched side chains (e.g., threonine, valine, isoleucine) and aromatic side chains (e.g., tyrosine, phenylalanine, tryptophan, histidine). Therefore, one or more amino acid residues in the CDR region or framework region of the antibody of the present invention can be replaced with other amino acid residues of the same side chain family, and the retained function of the modified antibody (variant antibody) can be tested.

Antibody fragments include, but are not limited to: (i) Fab fragments composed of $V_L$, $V_H$, $C_L$ and $C_{H1}$ domains, including Fab' and Fab'-SH; (ii) Fd fragments composed of $V_H$ and $C_{H1}$ domains; (iii) Fv fragment composed of $V_L$ and $V_H$ domains of a single antibody; (iv) dAb fragment composed of a single variable region (Ward et al., 1989, Nature 341: 544-546); (v) F(ab')$_2$ fragment, a bivalent fragment containing 2 linked Fab fragments; (vi) single-chain Fv molecule antigen binding site (Bird et al., 1988, Science 242: 423-426; Huston et al., 1988, Proc. Natl. Acad. Sci. USA 85: 5879-5883); (vii) bispecific single chain Fv dimer (PCT/US92/09965); (viii) "dibody" or "tribody", multivalent or multiple specific fragments (Tomlinson et al. 2000, Methods Enzymol. 326: 461-479; WO94/13804; Holliger et al. 1993, Proc. Natl. Acad. Sci. USA 90: 6444-6448); and (ix) ScFv genetically fused with identical or different antibodies (Coloma & Morrison, 1997, Nature Biotechnology 15, 159-163).

According to the constant region gene determination, antibodies are classified, also named as isotypes. Human constant light chains are divided into K (CK) and λ (Cλ) light chains. The heavy chain is divided into μ, δ, γ, α or ε, and the antibody isotypes IgM, IgD, IgG, IgA and IgE are defined. The IgG class is most commonly used for therapeutic purposes. In humans, this category includes subclasses IgG1, IgG2, IgG3 and IgG4. In mice, this category includes subclasses IgG1, IgG2a, IgG2b, and IgG3. IgM has subclasses, including but not limited to IgM1 and IgM2. IgA has several subclasses, including but not limited to IgA1 and IgA2. Accordingly, "isotype" as used herein refers to any class or subclass of immunoglobulin defined according to the chemical and antigenic characteristics of the constant region. Known isotypes of human immunoglobulin are IgG1, IgG2, IgG3, IgG4, IgA1, IgA2, IgM1, IgM2, IgD and IgE.

Anti-FAPα Antibody

In the present disclosure, antigen binding proteins (including antibodies) having scFv-based antigen binding regions are described. Among them, recombinant FAPα was used to select scFv from human scFv phage display library.

In some embodiments, the present invention includes an antibody having a scFv sequence, wherein scFv sequence is fused to one or more heavy chain constant regions to form an antibody with human immunoglobulin Fc regions for producing a bivalent protein, thereby increasing the overall affinity and stability of the antibody. In addition, the Fc moiety allows direct conjugation of other molecules (including but not limited to fluorescent dyes, cytotoxins, radioisotopes, etc.) with an antibody used in quantification studies of antigen, for example, to immobilize antibodies for affinity measurement, targeted delivery of therapy drugs, use immune effector cells to test Fc-mediated cytotoxicity, and many other applications.

The results provided herein highlight the specificity, sensitivity and utility of the antibodies of the invention when targeting FAPα.

The molecules of the present invention are based on the identification and selection of single-chain variable fragments (scFv) using phage display, the amino acid sequence of which provides the molecule with specificity for FAPα and forms the basis of all antigen-binding proteins of the present invention. Therefore, the scFv can be used to design a series of different "antibody" molecules, including, for example, full-length antibodies, fragments thereof such as Fab and F(ab')$_2$, fusion proteins (including scFv_Fc), multivalent antibodies, that is, an antibody with more than one specificities for the same antigen or different antigens, for example, bispecific T cell binding antibody (BiTE), tribodies, etc. (see Cuesta et al., Multivalent antibodies: when design surpasses evolution, Trends in Biotechnology 28: 355-362, 2010).

In one embodiment where the antigen binding protein is a full-length antibody, the heavy and light chains of the antibody of the invention may be of full-length (e.g., the antibody may include at least one, preferably two complete heavy chains, and at least one, preferably two complete light chains) or may include an antigen binding moiety (Fab, F(ab)$_2$, Fv or scFv). In other embodiments, the heavy chain constant region of an antibody is selected from, for example, IgG1, IgG2, IgG3, IgG4, IgM, IgA1, IgA2, IgD or IgE. The selection of antibody type will depend on the immune effector function to be triggered by the designed antibody. In constructing a recombinant immunoglobulin, suitable amino acid sequences for the constant regions of various immunoglobulin isotypes and methods for generating a wide variety of antibodies are known to a skilled person in the art.

In another aspect, the present invention provides an antigen binding unit that binds to FaPα, which includes a heavy chain variable region sequence selected from SEQ ID NOs: 11 or 15.

In another aspect, the present invention provides an antigen binding unit that binds to FaPα, which includes a light chain variable region sequence selected from SEQ ID NO: 13 or 17.

The heavy chain and light chain variable region sequences can be "mixed and matched" to produce an anti-FAPα binding molecule of the present invention, considering that each of these heavy chain and light chain variable region sequences can bind to FAPα.

In another aspect, the invention provides variants of antibodies that bind to FaPαor fragments thereof. Therefore, the present invention provides an antibody or fragment thereof having a heavy chain and/or light chain variable region that is at least 80% identical to the heavy chain or light chain variable region sequence of the antibody of the present invention. Preferably, the amino acid sequence identity of the heavy and/or light chain variable regions is at least 85%, more preferably at least 90%, most preferably at least 95%, 96%, 97%, 98%, 99%, including for example 80%, 81%, 82%, 83%, 84%, 85%, 86%, 87%, 88%, 89%, 90%, 91%, 92%, 93%, 94%, 95%, 96%, 97%, 98%, 99% and 100%.

Properties of Anti-FAPα Antibody

Standard assays to assess the binding ability of antibodies, such as anti-FAP antibodies are known in the art and include, for example, ELISA, Biacore, Western blot, and flow cytometry analysis. Suitable assays are described in detail in the examples.

Nucleic Acids, Vectors and Host Cells

The invention also provides an isolated nucleic acid encoding the antibody that bind to FaPα and fragments thereof, a vector and a host cell comprising the nucleic acid or vector. The nucleic acid can be located in whole cells, cell lysates, or in partially purified or substantially purified form.

The nucleic acid of the present invention can be obtained using standard molecular biology techniques. For example, standard PCR amplification or cDNA cloning techniques can be used to obtain cDNAs encoding light chains and heavy chains of antibodies or encoding VH and VL segments. For antibodies obtained from an immunoglobulin gene library (for example, using phage display technology), one or more nucleic acids encoding antibodies can be recovered from the library. Methods for introducing exogenous nucleic acids into host cells are generally known in the art and can vary with the used host cell.

For expressing a protein, the nucleic acid encoding the antibody of the present invention can be integrated into an expression vector. Various expression vectors can be used for expressing a protein. Expression vectors can include self-replicating extrachromosomal vectors, or vectors integrated into the host genome. Expression vectors used in the present invention include, but are not limited to, those by which a protein can be expressed in mammalian cells, bacteria, insect cells, yeast, and in vitro systems. As known in the art, various expression vectors are commercially or otherwise available, which can be used in the present invention to express antibodies.

Advantages of the Invention

1. The present invention provides antibodies that specifically bind to FAPα;

2. The present invention provides immune effector cells that specifically target FAPα; and 3. The antibody of the present invention can effectively bind to tumor cells expressing FAPα, and the immune effector cells of the present invention exhibit significant killing ability to FAP-expressing tumor cells.

The present invention will be further described below in conjunction with specific embodiments. It should be understood that these examples are only used to illustrate the present invention and not to limit the scope of the present invention. The experimental methods that do not indicate specific conditions in the following examples are generally performed under conditions described in J. Sambrook et al., Molecular Cloning Experiment Guide, Third Edition, Science Press, 2002, or according to conditions recommended by the manufacturer.

EXAMPLE 1

Preparation of FAPα Recombinant Protein

The Leu26-Asp760 gene of the extracellular segment of human FAPα was synthesized in vitro. A His tag was inserted at the C-terminus of the gene and connected with "GS" in the middle to form a fusion-expressed protein human FAPα_His (SEQ ID NO: 19). The corresponding gene sequence is shown in SEQ ID NO: 20.

A His tag was inserted at the C-terminus of in vitro synthezed mouse FAP extracellular segment gene (Leu26-Asp761), and connected with "GS" in the middle to form a fusion-expressed protein mouse FAPα_His (SEQ ID NO: 21). The corresponding gene sequence is shown in SEQ ID NO: 22.

293F cells were used to transiently transfect and express human FAPα_His and mouse FAPα_His respectively. The method of transfection can be found in the instruction manual of 293F cells. After transfection, affinity purification was performed through nickel column.

After purification, SDS-PAGE electrophoresis was performed. The results are shown in FIG. 1, the target protein with higher purity was obtained in E2.

After filtration through a 0.22 um membrane, a millipore ultrafiltration tube with a flow rate of 10KD was used for concentration, to obtaine a concentrated volume of less than 1 ml. A PD-Midi desalting column was used to collect human and murine FAPα recombinant proteins.

EXAMPLE 2

Screening scFv Specific for FAP Using a Fully Human Phage Display Library

The phage display library used in the present invention is a fully human natural scFv phage library constructed by the applicant, and the storage capacity is 1E+11. Using the screening method known to a skilled person in the art, 10 ug/ml antigen human FAPα was coated in the immune tube, and the phage library was added to the human FAPα-coated immune tube for 1.5 hours to screen and enrich scFv phage clones specifically binding to FAPα.

Figure 2:
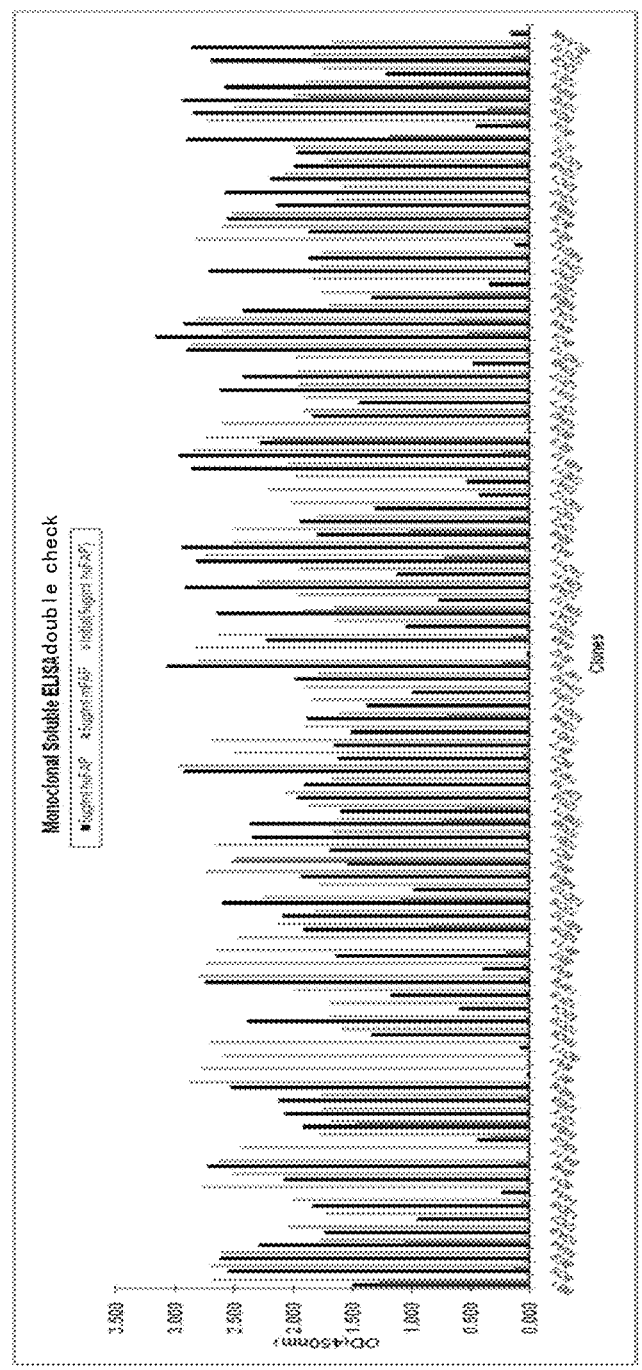
FIG. 2 shows the binding of expression supernatant of phage clone to recombinant huFAPα, mFAP by ELISA assay.

Positive clones were determined by standard ELISA method for FAPα. A total of 1344 clones were screened. 96 clones with the highest ELISA binding signal were selected (FIG. 2). After sequencing, 16 single sequences were obtained and these 16 clones were expressed, purified and measured for affinity was by Biacore. Results are shown in Table 1:

TABLE 1

Figure 3:
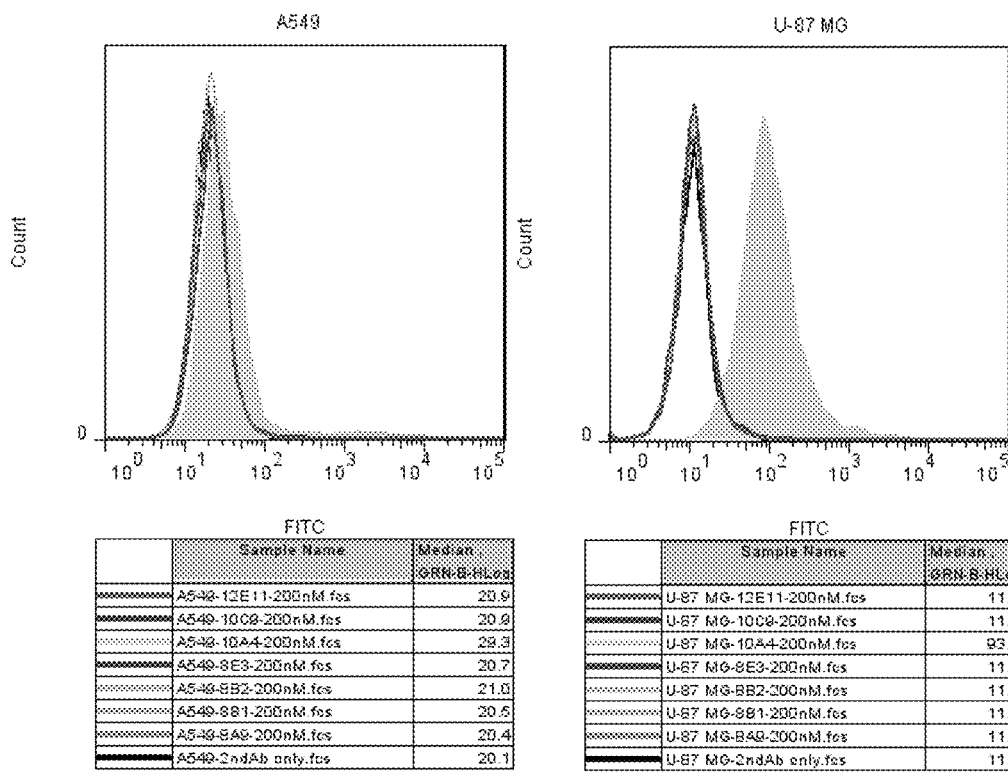
FIG. 3 shows the binding of partially purified clones to U-87MG and A549 cells detected by FACs.

| Ligand | ka (1/Ms) | kd (1/s) | KD (M) | Rmax (RU) | Chi$^2$ (RU$^2$) | Model |
|---|---|---|---|---|---|---|
| 12A6 | 1.39E+05 | 4.55E−03 | 3.28E−08 | 17.1 | 2.69 | 1:1 Binding |
| 8B8 | 3.76E+04 | 2.88E−03 | 7.64E−08 | 82.9 | 0.889 | 1:1 Binding |
| 8B1 | 4.19E+04 | 3.39E−03 | 8.08E−08 | 39.7 | 1.33 | 1:1 Binding |
| 10B9 | 5.08E+04 | 5.92E−03 | 1.17E−07 | 26.2 | 0.949 | 1:1 Binding |
| 8B2 | 5.49E+04 | 6.60E−03 | 1.20E−07 | 39.4 | 0.652 | 1:1 Binding |
| 12G12 | 5.93E+04 | 7.60E−03 | 1.28E−07 | 19.5 | 0.667 | 1:1 Binding |
| 10C9 | 3.27E+04 | 4.26E−03 | 1.30E−07 | 22.6 | 1.27 | 1:1 Binding |
| 8C4 | 2.74E+04 | 3.71E−03 | 1.35E−07 | 87.7 | 0.971 | 1:1 Binding |
| 10A3 | 3.18E+04 | 5.14E−03 | 1.62E−07 | 48.2 | 1.02 | 1:1 Binding |
| 10H7 | 3.84E+04 | 6.46E−03 | 1.68E−07 | 37.4 | 0.573 | 1:1 Binding |
| 8E3 | 3.56E+04 | 6.21E−03 | 1.74E−07 | 42.1 | 1 | 1:1 Binding |
| 10A4 | 1.94E+04 | 3.81E−03 | 1.96E−07 | 47 | 1.63 | 1:1 Binding |
| 8A3 | 1.98E+04 | 6.76E−03 | 3.42E−07 | 112.4 | 1.74 | 1:1 Binding |
| 12E11 | 1.58E+04 | 6.36E−03 | 4.03E−07 | 65.2 | 1.15 | 1:1 Binding |
| 8A9 | 7.53E+03 | 6.12E−03 | 8.13E−07 | 131.3 | 0.761 | 1:1 Binding | antibodies binding to U-87MG cells (purchased from the Chinese Academy of Sciences) endogenously expressing FAPα was detected by FACs, and A549 cells (purchased from the Chinese Academy of Sciences) not expressing FAPα were used as negative control cells. Guava easyCyte™ HT System instrument was used, the results are shown in FIG. 3 which shows that the antibody 10A4 specifically binds to U-87MG cells.

After sequencing analysis, the heavy chain variable region of 10A4 is the sequence as shown in SEQ ID NO: 11, and the sequences of the heavy chain HCDR1, HCDR2, and HCDR3 are shown in SEQ ID NO: 1, 2, and 3, respectively. The light chain variable region of 10A4 is the sequence as shown in SEQ ID NO: 13, and the sequences of the light chain LCDR1, LCDR2, and LCDR3 are shown in SEQ ID NO: 4, 5, and 6, respectively.

EXAMPLE 3

Construction of Affinity Mature Library of Antibody 10A4 and Screening Affinity Mature Library The construction of the affinity mature library based on antibody 10A4 retained the CDR3 regions of the light chain and the heavy chain. The CDR1 and CDR2 of the light chain or the CDR1 and CDR2 of the heavy chain were randomized using degenerate primers, respectively to construct two affinity mature libraries. The specific construction method is briefly described as follows:

First, a template plasmid was constructed based on the scFv of the antibody 10A4 (amino acid sequence SEQ ID NO: 23, nucleotide sequence SEQ ID NO: 24). For the phage libraries of the light chain CDR1 and CDR2 randomization, primers LMF (SEQ ID NO: 41) and F1OL1R (SEQ ID NO: 45) were used to PCR-amplify fragment 1; primers F10L2F (SEQ ID NO: 46) and FdR (SEQ ID NO: 44) were used to PCR-amplify fragment 2; fragment 1 and fragment 2 were connected by bridging PCR to obtain the full-length scFv containing randomized sequence, and then the full-length fragment was digested with NcoI and NotI, ligated into the template plasmid digested by the same enzyme through T4 ligase, and transformed into TG1 competent cells with a storage capacity of 1.5E+9. For the phage libraries of heavy chain CDR1 and CDR2 randomization, primers LMF (SEQ ID NO: 41) and F10H1R (SEQ ID NO: 42) were used to PCR-amplify fragment 3; primers F10H2F (SEQ ID NO: 43) and FdR (SEQ ID NO: 44) were used to PCR-amplify fragment 4; fragment 3 and fragment 4 were connected by bridging PCR to obtain the full-length scFv containing the randomized sequence, and then the full-length fragment was digested with NcoI and NotI, connected into the template plasmid digested by the same enzyme with T4 ligase, and transformed into TG1 competent cells with a storage capacity of 6.6E+8.

The screening of affinity mature libraries is substantially the same as the description in Example 2. 5 ug/ml or 1 ug/ml antigen human FAPα was coated in the immune tube, and the phage library was added to the human FAPα-coated immune tube for binding for 1.5 hours. After screening and enrichment, a scFv phage clone specifically binding to human FAPα was obtained.

Figure 4:
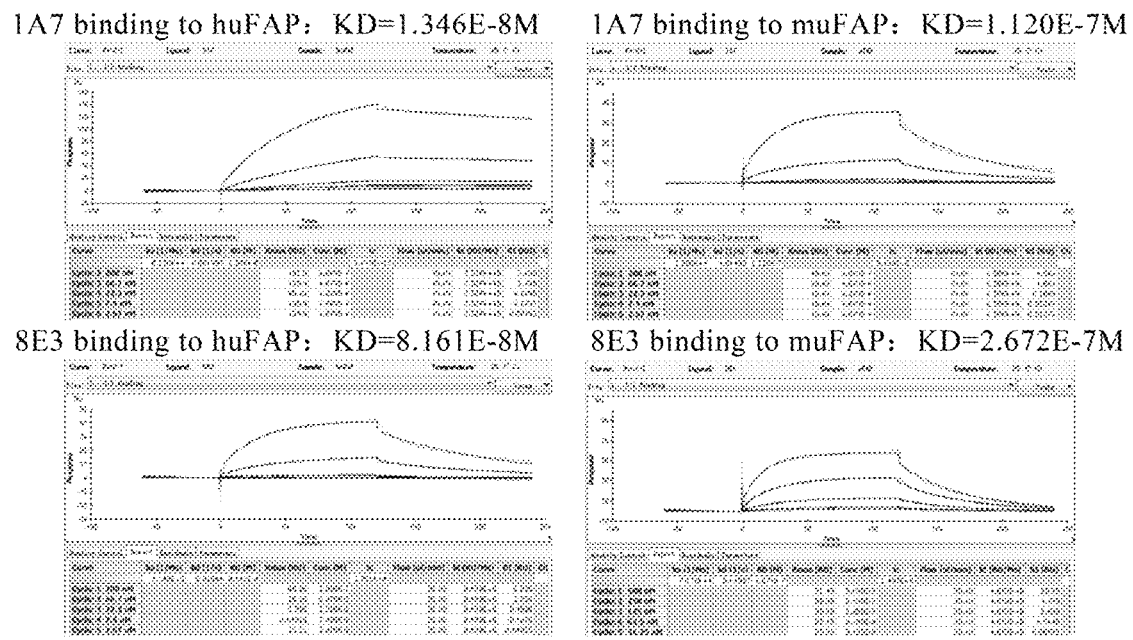
FIG. 4 shows the affinities of 1A7, 8E3 (scFv) binding to huFAP and mFAP determined by Biacore assay.

Positive clones were determined by standard ELISA method, and clones with high ELISA signal were selected for expression and purification. Two obtained clones (1A7, 8E3) performed better than the parent antibody 10A4 determined by Biacore (see FIG. 4). The affinity of parent antibody 10A4 for human FAPα is 197 nM (as shown in FIG. 4); the affinity of antibody 1A7 for human FAPα is 13.5 nM, which is 14 times higher than that of 10A4; and the affinity of antibody 8E3 for human FAPα is 81.6 nM, which is 2.4 times higher than that of 10A4. Both antibodies can bind to murine FAP with an affinity of 112 nM and 267 nM, respectively.

1A7 and 8E3 were sequenced. The sequencing results showed that, compared with the parent antibody 10A4, there are a total of 7 point mutations in antibody 1A7, in which 2 mutations are located in the CDR1 of the heavy chain, Ser to Pro at the $31^{st}$ position, and Ala to Thr at the $33^{rd}$ position; 5 mutations were located in the CDR2 of the heavy chain, Ile to Val at the $52^{nd}$ position, Ile to Asn at the $54^{th}$ position, Phe to Val at the $55^{th}$ position, and Thr to Val at the $57^{th}$ position, and Asn to Thr at the $59^{th}$ position. There are a total of 6 point mutations in Antibody 8E3, in which 4 mutations are located in the CDR1 of the light chain, Ser to Pro at the $32^{nd}$ position, Tyr to Phe at the $35^{th}$ position, Tyr to His at the $37^{th}$ position, and Asp to Tyr at the $39^{th}$ position; and there are 2 mutations are located in the CDR2 of the light chain, Leu to Val at the $55^{th}$ position, and Ser to Gly at the $57^{th}$ position.

Figure 5:
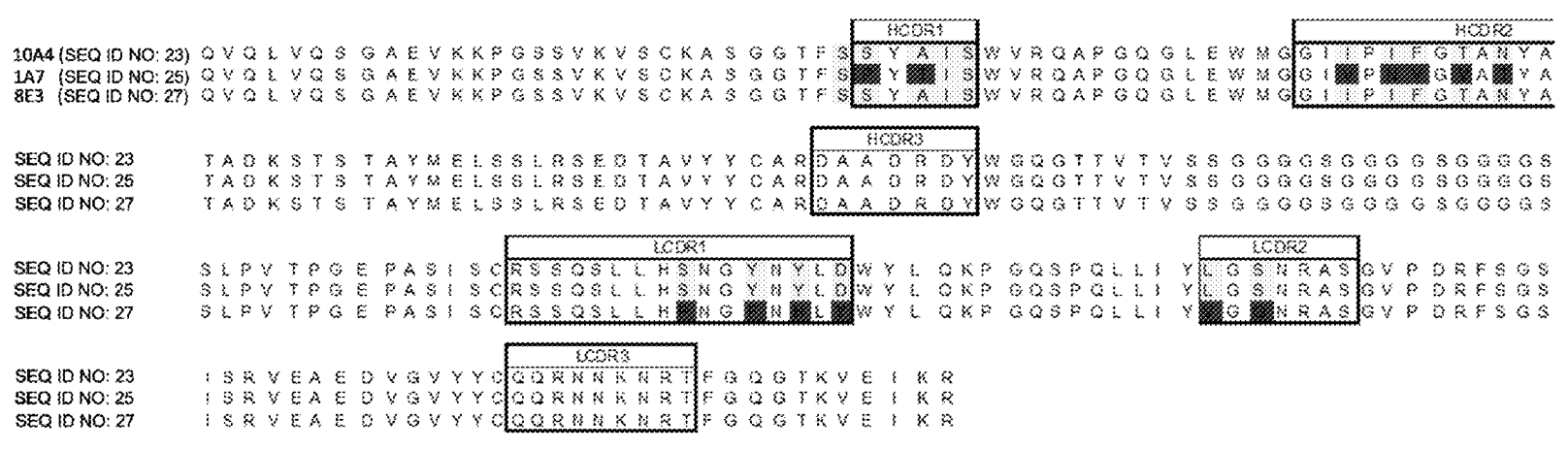

The results of sequence alignment are shown in FIG. 5, and the comparison of antibody identities found that comparing 1A7 with 10A4, there is 60% similarity between the sequences of CDR1 of the heavy chain, there is 70.5% similarity between the sequences of CDR2 of the heavy chain, there is 100% similarity between the sequences of CDR3 of the heavy chain, and there is 93.9% similarity between the heavy chain variable regions (116 amino acids in total, in which 7 is different); comparing 8E3 with 10A4, there is 75% similarity between the sequences of the light chain CDR1 (16 amino acids in total, in which 4 is different), there is 71.4% similarity between the light chain CDR2 (7 amino acids in total, in which 2 is different), there is 100% similarity between the light chain CDR3, and there is 94.6% similarity between the light chain variable regions (113 amino acids in total, in which 6 is different).

EXAMPLE 4

Figure 6:
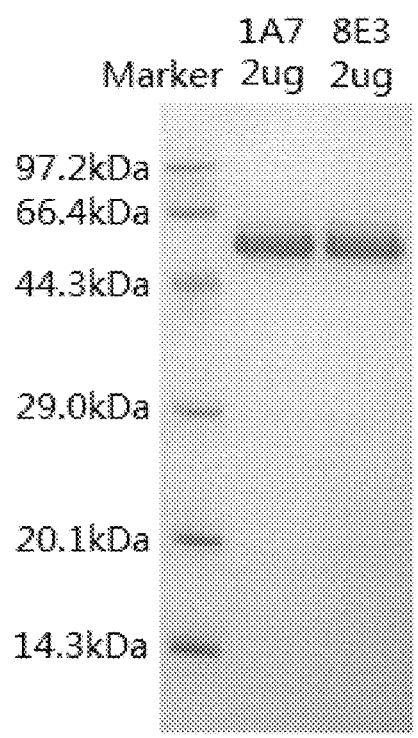
FIG. 6 is the analysis of purified antibodies 1A7, 8E3 (scFv_Fc) by SDS PAGE.

Construction of scFv-Fc Fusion Antibody and Transient Expression and Purification Thereof in Eukaryotic Cells Primers for $V_H$ and $V_L$ fragments of 10A4, 1A7 and 8E3 were designed, respectively, and a linker consisting of 15 flexible amino acids (GGGGSGGGGSGGGGS) was introduced to form scFv (10A4, SEQ ID NO: 23; 1A7, SEQ ID NO: 25; 8E3, SEQ ID NO: 27); the cleavage site of Nhe I and protective bases were introduced upstream to $V_H$; the cleavage site of BamHI and protective bases were introduced downstream to $V_L$. The PCR product was analyzed by 1% agarose gel electrophoresis, purified and recovered. After digestion, it was ligated into a V152 (purchased from Shanghai Ruijin Biotechnology Co., Ltd.) eukaryotic expression vector containing Fc segment Asp104-Lys330 of human IgG1 heavy chain constant region. 293F cells in the logarithmic growth phase were transiently transfected with 293fectin™ Transfection reagent (Invitrogen, 12347-019) or polyethyleneimine (PEI) (Sigma-Aldrich, 408727). 5-7 days after transfection, the culture supernatant was collected and purified by Protein A for affinity purification. The purified product was analyzed through SDS PAGE, as shown in FIG. 6, under reducing conditions, and the band size was 50kD, as expected.

EXAMPLE 5

Construction of HT1080-huFAPα, 3T3-mFAP Stably Transfected Cell Line

1. Construction of lentiviral packaging plasmids pWPT-huFAPα_Flag, pWPT-mFAP_Flag The full-length sequence of huFAPα was synthesized in vitro, and a Flag tag (SEQ ID NO: 29) was inserted at the C-terminus, digested by MluI/SalI double digestion, and inserted into lentiviral packaging plasmid pWPT double digested by the same enzymes. The full-length sequence of mFAPα was synthesized in vitro, and a Flag tag (SEQ ID NO: 30) was inserted at the C-terminus, double digested by MluI/SalI, and inserted into lentiviral packaging plasmid pWPT double digested by the same enzymes.

2. Preparation of mFAP Virus Liquid and huFAPα Virus Liquid

6×106 cells were inoculated into a petri dish and subjected to transfection when the cell confluence was 70%-80%. The 293T medium was replaced with complete medium 1 h before transfection. 800 ul DMEM was added to a EP tube, and then 5 ug of pWPT-mFAP-Flag plasmid, 7.5 ug psPAX.2 plasmid and 2.5 ug pMD2.G plasmid were added and vortexed for 8 s. 800 ul of DMEM and 45 uL of 1 ug/ul PEI were added in another EP tube and placed for 5 minutes at room temperature. The plasmid mixture was added dropwise to the PEI incubation solution, mixed and allowed to stand at room temperature for 20 minutes. Then the formulated plasmid/PEI mixture was added dropwise to the cells. Six hours after transfection, the medium was replaced with fresh complete medium. 72 hours after transfection, the cell culture supernatant was collected, and centrifuged at 3000 rpm for 15 minutes at 4°. The supernatant was taken and filtered through a 0.45 um filter to obtain mFAP virus liquid.

The preparation method for huFAP virus liquid is the same as that for mFAP virus liquid.

3. Virus-Infected Cells

On the first day, 1×10⁵ 3T3 cells were inoculated iton a 6 cm Petri dish. The next day, the supernatant was discarded and 1 ml of fresh complete medium was added, followed by 4 ml of mFAP virus liquid and polybrene with a final concentration of 6 ug/ml for culture to obtain 3T3-huFAP mixed clone cells.

HT1080 cells were infected with huFAPα virus, and 3T3 cells were infected with mFAP virus liquid.

4. Identification of 3T3-mFAP and HT1080-huFAPα Mixed Clone by Western Blotting

Figure 7:
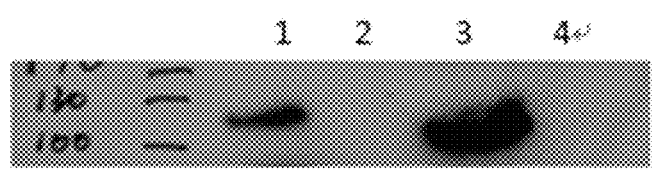
FIG. 7 shows the results of cell lines stably-transfected with 3T3-mFAP and HT1080-huFAPα detected by Western blot.

Cells in 3T3-huFAP mixed clones or cells in HT1080-huFAPα mixed clones were lysed with protein lysate. After centrifugation, the supernatant was taken for BCA concentration determination. 3T3 was used as a negative control. Primary antibody: anti-FLAG-HRP (M2), 1: 400 dilution. The results are shown in FIG. 7.

5. Flow Cytometry Detection

Figure 8A:
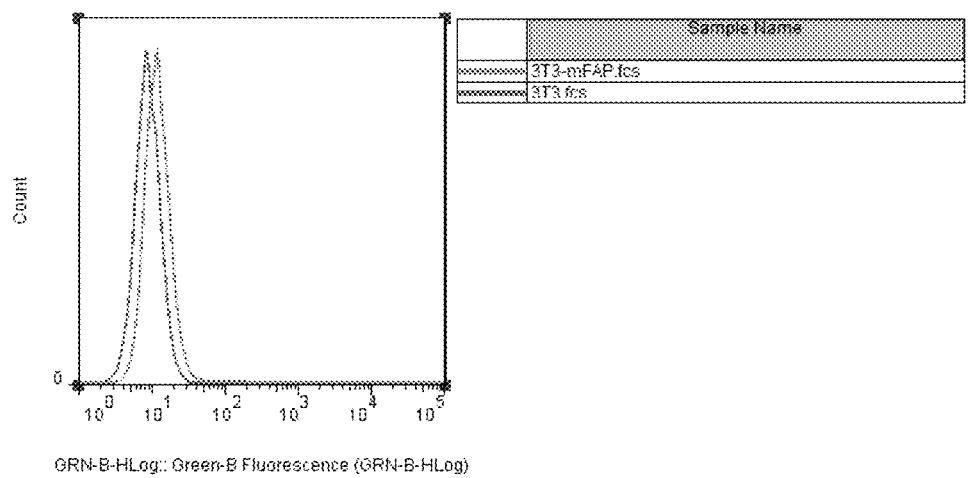
FIG. 8 shows the results of cell lines stably-transfected with 3T3-mFAP (a) and HT1080-huFAPα (b) detected by FACs.
Figure 8B:
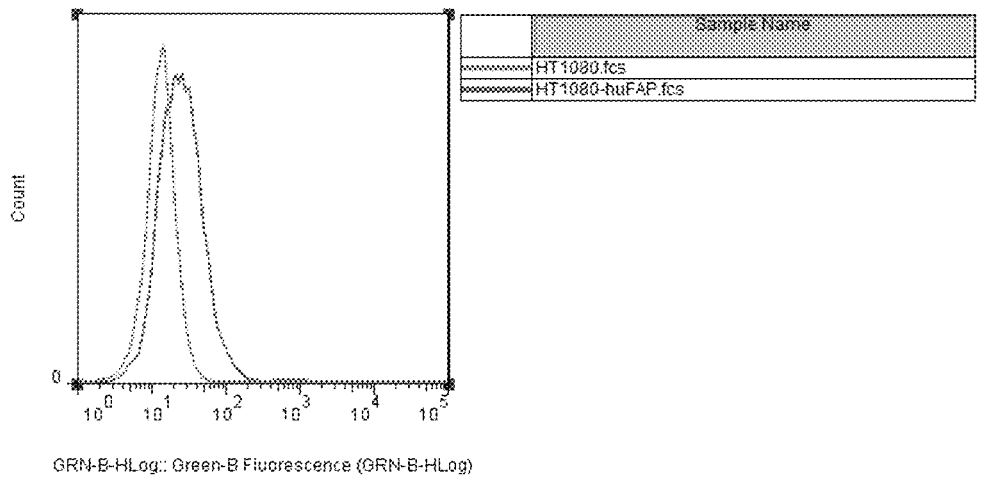

Cells in the mixed clones of HT1080-huFAPα and 3T3-mFAP were digested and counted respectively, and the monoclonal plating was performed by limiting dilution method to obtain the stably transfected cell lines of HT1080-huFAPα and 3T3-mFAP. 4×10⁵ cells were taken for flow cytometry detection by using Guava easyCyte™ HT System. The results are shown in FIG. 8. FAP expression was detected in both stably transfected cell lines.

Figure 10A:
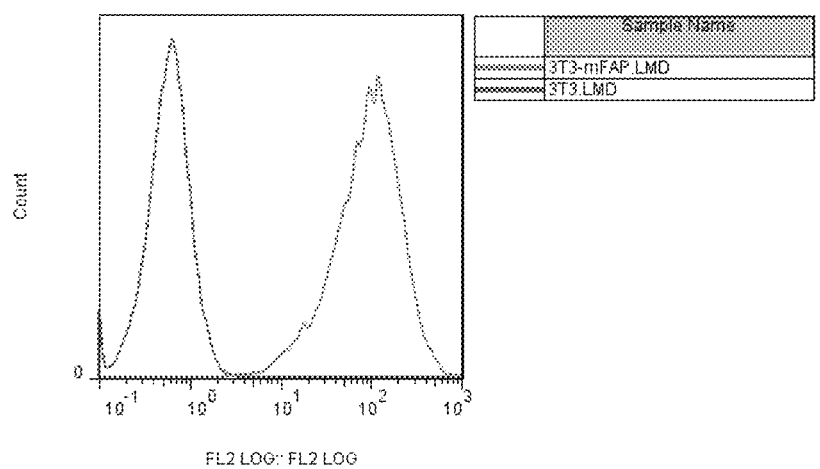
FIG. 10 shows the expression of mFAPα and huFAPα in cell lines stably-transfected with 3T3-mFAP (a) and HT1080-huFAP (b) detected by FACs using Anti-Flag antibody.
Figure 10B:
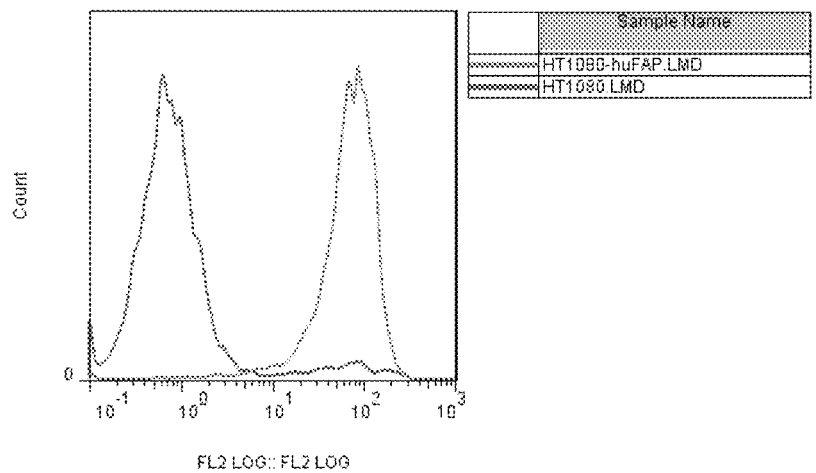

3T3-mFAP, HT1080-huFAPα cell line was detected using Anti-Flag antibody through flow cytometry. 1×10⁶ cells were taken for flow cytometry. The results are shown in FIG. 10. By detecting the Flag tag on FAP, the expression of FAP was detected in both of stably transfected cell lines.

EXAMPLE 6

Binding of scFv-Fc of Antibodies 10A4, 1A7, 8E3 to U-87MG, 3T3-mFAP, HT1080-huFAPα Cells by FACs Determination 3T3 cells and HT1080 cells were used as negative control cells. Particular steps are listed as follows: cells were harvested, washed once with growth medium, and resuspended in PBS. The cell concentration was adjusted to 4E+5 cells/ml. The 200 nM antibody was incubated with the cells for 30 minutes on ice. Afterwards, it was incubated with a FITC-labeled anti-human IgG secondary antibody. After washed for two times, the Guava easyCyte™ HT System instrument was used for detection.

Figure 9:
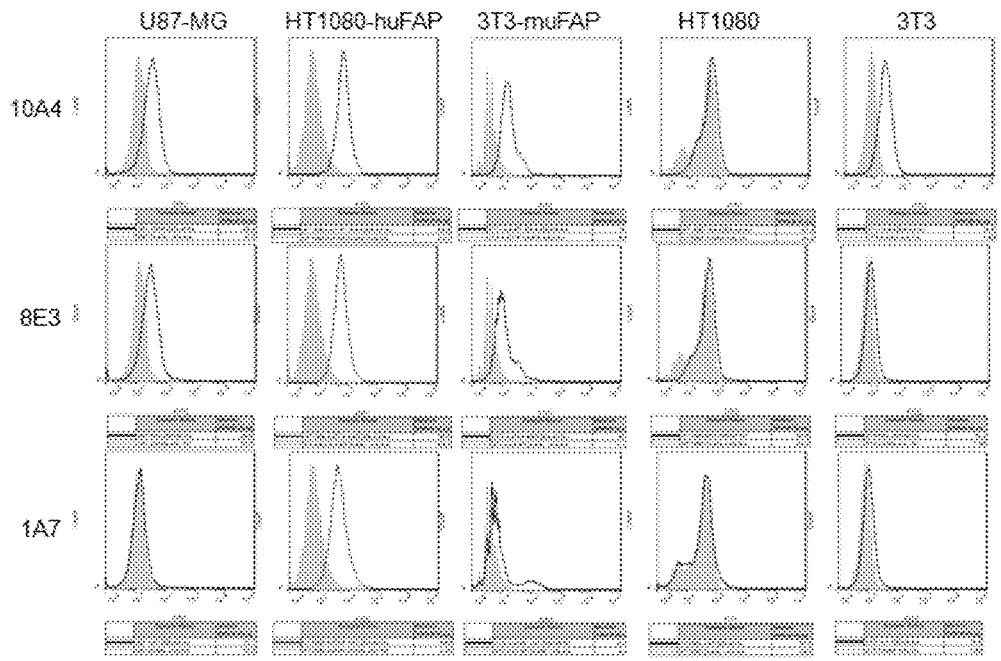
FIG. 9 shows the binding of antibodies 10A4, 1A7, 8E3 (scFv_Fc) to U-87MG, 3T3-mFAP, HT1080-huFAPα cells determined by FACs.

The results are shown in FIG. 9. Antibody 10A4 can bind HT1080 cell line stably transfected with huFAPα, 3T3 cell line stably transfected with mFAP and U-87MG cells endogenously expressing huFAPα, but not bind HT1080 cell line that do not express huFAPα, and non-specifically bind to 3T3 cell line. Antibody 8E3 did not bind to the negative cell lines 3T3 and HT1080, but binds to the cell lines HT1080-huFAPα, 3T3-mFAP and U-87MG positive for FAP expression. Antibody 1A7 did not bind to the negative cell lines 3T3 and HT1080, bound to HT1080-huFAPα and 3T3-mFAP, but did not bind to U-87MG cells.

EXAMPLE 7

Preparation of Chimeric Antigen Receptor (CAR) Modified T cells Targeting FAPa

1. Construction of lentiviral packaging plasmid pRRL-hu8E3-28Z

Lentiviral plasmid expressing a second-generation chimeric antigen receptor of antibodies 10A4, 1A7, 8E3 was constructed by using PRRLSIN-cPPT.EF-1α as a vector, including PRRLSIN-cPPT.EF-1α-10A4-28Z, PRRLSIN-cPPT EF-1α-1A7-28Z and PRRLSIN-cPPT.EF-1α-8E3-28Z. 10A4-28Z sequence consists of CD8α signal peptide (SEQ ID NO: 32), 10A4 scFv (SEQ ID NO: 24), CD8 hinge (SEQ ID NO: 34), CD28 transmembrane region (SEQ ID NO: 36), intracellular signaling domain (SEQ ID NO: 38) and intracellular segment CD3 of CD3 (SEQ ID NO: 40); 1A7-28Z sequence consists of CD8λ signal peptide (SEQ ID NO: 32), 1A7 scFv (SEQ ID NO: 26), CD8 hinge (SEQ ID NO: 34), CD28 transmembrane region (SEQ ID NO: 36), intracellular signaling domain (SEQ ID NO: 38) and intracellular segment CD3ζ of CD3 (SEQ ID NO: 40); and 8E3-28BB sequence consiss of CD8α signal peptide (SEQ ID NO: 32), 8E3-scFv (SEQ ID NO: 28), CD8 hinge (SEQ ID NO: 34), CD28 transmembrane region (SEQ ID NO: 36), intracellular signaling domain (SEQ ID NO: 38) and intracellular segment CD3 of CD3 (SEQ ID NO: 40).

2. Packaging hu8E3-28Z lentivirus by plasmid-transfected 293T cells a) 293T cells were taken for digestion, then spreaded into a 15 cm dish at 1.25×10⁷, cultured at 37° C. until the cell confluence was 70% -80%, and the supernatant was replaced with 10 mL of fresh 10% FBS medium.

b) Preparation of plasmid/PEI mixture pRRL-hu8E3-28Z 13.7ug, pVSV.G 6.3 ug, RRE 16.4 ug, REV 16.4 ug were taken, and added into 2200 uL DMEM for incubation. 165 ul of corresponding amount of PEI (1 ug/ul) was added into 2200 uL DMEM and incubated for 5 min. The mixed liquid of plasmid was added into PEI incubation liquid, mixed well, and incubated at room temperature for 20 min to obtain the plasmid/PEI mixture.

c) the plasmid/PEI mixed liquid prepared in b) was added dropwise to the cells of a), and mixed well. After 5 h, the liquid was changed. After 72 h, the virus supernatant was collected, and filtered through a 0.45 um filter. PEG8000 was added, purified at 4° C. overnight, and centrifuged at 4000 rpm and 4° C. Virus pellet was collected to obtain hu8E3-28Z lentivirus.

3. T cells infected by recombinant human lentivirus a) PBMCs were cultured in AIM-V medium (Gibco, # 0870112) +2% human AB serum (Gemini, # 100-512), recombinant human IL-2 (500 U/ml) (Shanghai Huaxin Biotech Co., Ltd.) was added, and CD3/CD28 magnetic beads (Invitrogen, # 21013) were added at a ratio of 1: 1 (cell: magnetic beads) to activate T cells. After 48 hrs, cells were infected.

b) A plate was coated with Retronectin (Takara, # T100A) at 4° C. overnight at a concentration of 5 μg/ml. Activated T cells were added into the Retronectin-coated plate at a density of 1×10⁶ cells/ml. The high-purity virus collected in step 2 (MOI≈10) were added, centrifuged at 1800 rpm and 32° C. for 40 min, place into an incubator for 48 hours. The medium was changed (AIM-V medium +2% human AB serum, IL-2 500U/ml), the magnetic beads were removed, and then the cells were cultured at a density of 5×10⁵ cells/ml for 6-10 days, as as to obtain T cells infected with hu8E3-28Z virus, that is, T cells expressing 8E3-28Z (SEQ ID NO: 48).

Figure 11:
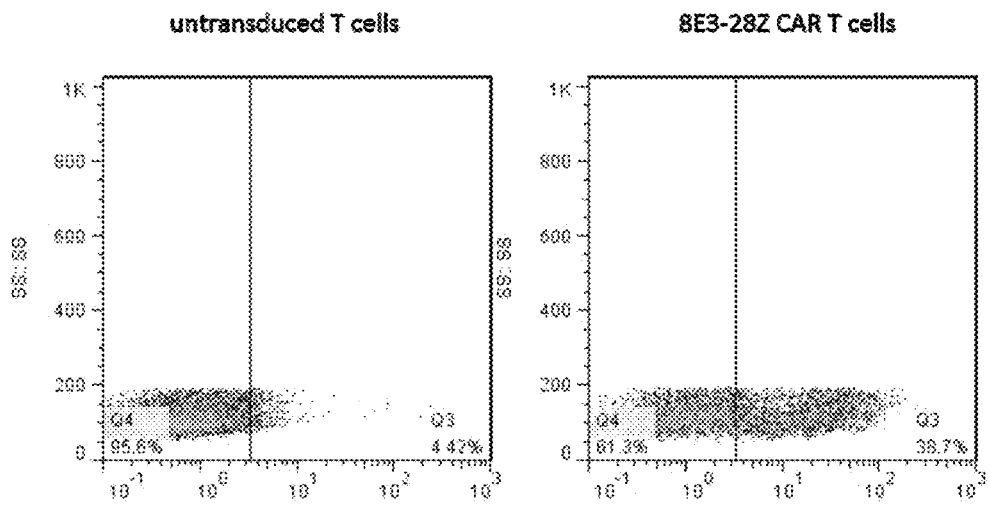
FIG. 11 shows the expression of hu8E3-28Z CAR in T cells detected by FACs.

5×10⁵ 8E3-28Z T cells and virus-free T cells were taken for flow cytometry to detect the expression of 8E3-28Z CAR in T cells. The detection instrument was Beckman Coulter Epics XL Flow Cytometer. The results are shown in FIG. 11, which shows that hu8E3-28Z CAR expression can be detected in T cells infected with hu8E3-28Z virus.

Example 8

Detection of Cytotoxicity of CAR T Cells with 8E3-28Z

The hu8E3-28Z T cells prepared in Example 8 were taken to detect the killing effects on 3T3-mFAP and H1080-huFAPα cells, and the method is listed as follows:

The 3T3-mFAP monoclonal cells were digested and counted, and the T cells expressing 8E3-28Z CAR were centrifuged and counted. 3T3-mFAP cells were used as target cells, and effector cells were T cells expressing 8E3-28Z CAR. The effective target ratios were 3: 1, 1: 1, 1: 3, and the number of target cells was 10000/well, and different numbers of effector cells (i.e., 30000/well, 10000/well, 3333/well) were set according to different effect target ratios. Wells in quintuplicate were set for each group. After incubation for a total of 18 hours, the amount of LDH in the supernatant was detected by CytoTox96 non-radioactive cytotoxicity kit (Promega, #G1780), and the killing activities were calculated (details can be found in the instruction of CytoTox96 Non-Radioactive Cytotoxicity Kit). The toxicity test of killing effects of T cells expressing 8E3-28Z CAR on 3T3, H1080 and H1080-huFAPα cells was the same as that of 3T3-mFAP cells.

Figure 12A:
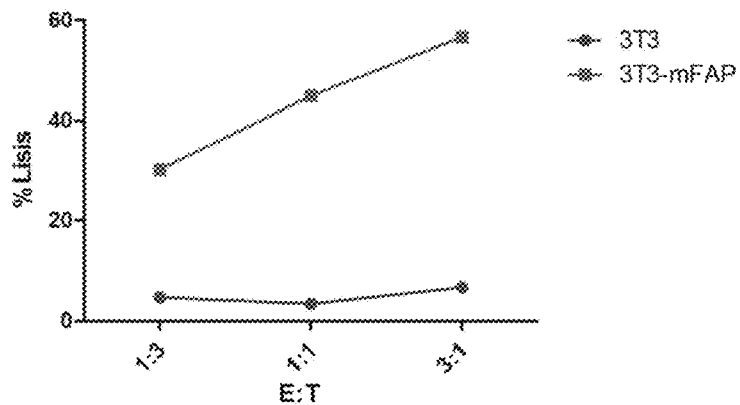
FIG. 12 shows the killing of T cells expressing hu8E3-28Z CAR on 3T3-mFAP (a) and H1080-huFAPα (b) cells detected by cytotoxicity assay.
Figure 12B:
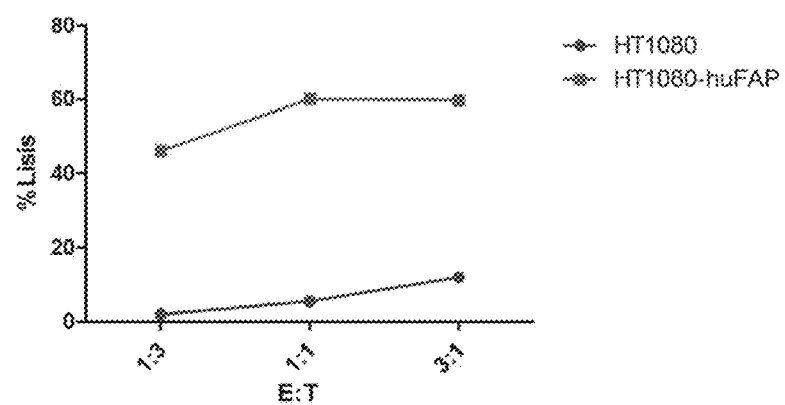

As shown in FIG. 12, T cells expressing 8E3-28Z CAR can specifically kill 3T3-mFAP cells expressing mouse FAPα and H1080-huFAPα cells expressing human FAPα.

All documents mentioned in the present invention are incorporated by reference in this application, as if each document was individually incorporated by reference. In addition, it should be understood that after reading the above teaching content of the present invention, a skilled person in the art can make various changes or modifications to the present invention, and these equivalent forms also fall within the scope defined by the claims appended to this application.

The invention claimed is:

1. An antigen binding unit for targeting fibroblast activation protein alpha (FAPα), comprising: a light chain variable region and a heavy chain variable region,
wherein the heavy chain variable region comprises HCDR1, HCDR2, and HCDR3, and the light chain variable region comprises LCDR1, LCDR2, and LCDR3;
the HCDR1 has the sequence as shown in SEQ ID NO: 1 or 7,
the HCDR2 has the sequence as shown in SEQ ID NO: 2 or 8,
the HCDR3 has the sequence as shown in SEQ ID NO: 3,
the LCDR1 has the sequence as shown in SEQ ID NO: 4 or 9,
the LCDR2 has the sequence as shown in SEQ ID NO: 5 or 10, and
the LCDR3 has the sequence as shown in SEQ ID NO: 6.

2. The antigen binding unit of claim 1, wherein the sequences of HCDR1, HCDR2 and HCDR3 are selected from any one of the following groups:
 (a) SEQ ID NO: 1, SEQ ID NO: 2, SEQ ID NO: 3; and
 (b) SEQ ID NO: 7, SEQ ID NO: 8, SEQ ID NO: 3.

3. The antigen binding unit of claim 1, wherein the sequences of LCDR1, LCDR2, and LCDR3 are selected from any one of the following groups:
 (a) SEQ ID NO: 4, SEQ ID NO: 5, SEQ ID NO: 6; and
 (b) SEQ ID NO: 9, SEQ ID NO: 10, SEQ ID NO: 6.

4. The antigen binding unit of claim 1, wherein the HCDR1 comprises the sequence as shown in SEQ ID NO: 1, the HCDR2 comprises the sequence as shown in SEQ ID NO: 2, the HCDR3 comprises the sequence as shown in SEQ ID NO: 3, the LCDR1 comprises the sequence as shown in SEQ ID NO: 4, the LCDR2 comprises the sequence as shown in SEQ ID NO: 5, and the LCDR3 comprises the sequence as shown in SEQ ID NO: 6; or the HCDR1 comprises the sequence as shown in SEQ ID NO: 7, the HCDR2 comprises the sequence as shown in SEQ ID NO: 8, the HCDR3 comprises the sequence as shown in SEQ ID NO: 3, the LCDR1 comprises the sequence as shown in SEQ ID NO: 4, the LCDR2 comprises the sequence as shown in SEQ ID NO: 5, and the LCDR3 comprises the sequence as shown in SEQ ID NO: 6; or the HCDR1 comprises the sequence as shown in SEQ ID NO: 1, the HCDR2 comprises the sequence as shown in SEQ ID NO: 2, the HCDR3 comprises the sequence as shown in SEQ ID NO: 3, the LCDR1 comprises the sequence as shown in SEQ ID NO: 9, the LCDR2 comprises the sequence as shown in SEQ ID NO: 10, and the LCDR3 comprises the sequence as shown in SEQ ID NO: 6.

5. The antigen binding unit of claim 1, wherein the antigen binding unit has a heavy chain variable region as shown in SEQ ID NO: 11 or 15, and a light chain variable region as shown in SEQ ID NO: 13 or 17.

6. The antigen binding unit of claim 1, wherein the antigen binding unit is a monoclonal antibody, a fully human antibody, a humanized antibody, or a chimeric antibody.

7. The antigen binding unit of claim 1, wherein the antigen binding unit is scFv, Fv, Fab, (Fab)$_2$, or single domain antibody.

8. A bivalent protein, which is an antibody having a human immunoglobulin Fc region formed by fusing the scFv sequence of claim 7 with a human heavy chain constant region.

9. A multifunctional immunoconjugate, wherein the multifunctional immunoconjugate includes:
 the antigen binding unit of claim 1, and a functional molecule connected thereto.

10. A chimeric antigen receptor, wherein the extracellular domain of the chimeric antigen receptor comprises the antigen binding unit of claim 1.

11. The chimeric antigen receptor of claim 10, wherein the chimeric antigen receptor comprises an antibody, a transmembrane region and an intracellular signal region connected in the following order:
 the antigen binding unit, CD8 and CD3ζ;
 the antigen binding unit, CD8, CD137 and CD3ζ;
 the antigen-binding unit, the transmembrane region of CD28 molecule, the intracellular signal region of CD28 molecule and CD3ζ; or
 the antigen binding unit, the transmembrane region of CD28 molecule, the intracellular signal region of CD28 molecule, CD137 and CD3ζ.

12. A pharmaceutical composition comprising the antigen binding unit of claim 1.

* * * * *